United States Patent [19]

Testa et al.

[11] Patent Number: 5,503,828
[45] Date of Patent: Apr. 2, 1996

[54] ALPHA INTERFERON COMPOSITION AND METHOD FOR ITS PRODUCTION FROM HUMAN PERIPHERAL BLOOD LEUKOCYTES

[75] Inventors: Douglas Testa, Neshanic Station; Mei-June Liao, Monmouth Junction; Katalin Ferencz-Biro, North Brunswick; Abbas Rashidbaigi, Morris Plains, all of N.J.; Mario DiPaola, Bayside, N.Y.; Manisha Padhye, North Brunswick, N.J.

[73] Assignee: Interferon Sciences, Inc., New Brunswick, N.J.

[21] Appl. No.: 129,089

[22] PCT Filed: Feb. 9, 1993

[86] PCT No.: PCT/US93/01135

§ 371 Date: Oct. 5, 1993

§ 102(e) Date: Oct. 5, 1993

[87] PCT Pub. No.: WO93/16107

PCT Pub. Date: Aug. 19, 1993

Related U.S. Application Data

[63] Continuation-in-part of Ser. No. 835,030, Feb. 10, 1992, abandoned.

[51] Int. Cl.$^6$ .................................................. A61K 38/21
[52] U.S. Cl. .......................... 424/85.7; 424/85.4; 514/2; 514/21; 530/351
[58] Field of Search .................................. 424/85.4, 85.7; 514/2, 21; 530/351

[56] References Cited

U.S. PATENT DOCUMENTS

| | | | |
|---|---|---|---|
| 4,289,690 | 9/1981 | Pestka et al. | 424/85.4 |
| 4,503,035 | 3/1985 | Pestka et al. | 424/85.4 |
| 4,530,901 | 7/1985 | Weissmann | 435/70 |
| 4,636,383 | 1/1987 | Nagabhushan et al. | 424/85.4 |
| 4,656,131 | 4/1987 | Kitano et al. | 435/68 |
| 4,696,899 | 9/1987 | Toth et al. | 435/68 |
| 4,780,530 | 10/1988 | Teraoka et al. | 530/351 |
| 4,791,101 | 12/1988 | Adolf | 514/2 |
| 4,820,514 | 4/1989 | Cummins | 424/85.4 |
| 4,911,908 | 3/1990 | Estis et al. | 424/85.4 |

FOREIGN PATENT DOCUMENTS

| | | |
|---|---|---|
| 018218 | 10/1980 | European Pat. Off. . |
| 091543 | 10/1983 | European Pat. Off. . |
| 83/00693 | 3/1983 | WIPO . |
| WO93/16107 | 8/1993 | WIPO . |

OTHER PUBLICATIONS

Fish et al., Biochem & Biophy Res Comm., vol. 112 No. 2, pp. 537–546, 1983.

Product Information, ALFERON® N Injection, Interferon alfa-n3 (Human Leukocyte Derived) (1989).

K. Berg et al, "Purification of Human Interferon by Antibody Affinity Chromatography, using Highly Absorbed Anti-interferon," Scan. J. Immunol., 8:429–436 (May 1978).

L. S. Lin and W. E. Stewart II, "Purification of Human Leukocyte Interferon by Two-Dimensional Polyacrylamide Gel Electrophoresis," Meth. Enzymol., 78:481–487 (Dec. 18, 1981).

L. S. Lin et al, "Purification of Human Leukocyte Interferon to Apparant Homogeniety: Criteria for Purity," Abstr. Ann. Meeting American Soc. for Microbiol., S203 (14–19 May 1978).

S. Pestka, "The Human Interferons—From Protein Purification and Seuqence to Cloning and Expression in Bacteria: Before, Between, and Beyond," Arch. Biochem. Biophys., 221(1):1–37 (Feb. 15, 1983).

L. S. Lin et al, "Characterization of the Heterogeneous Molecules of Human Interferons: Differences in the Cross-Species Antiviral Activities of Various Molecular Populations in Human Leukocyte Interferons," J. Gen. Virol. 39:125–130 (1978).

K. Weber and D. J. Kuter, "Reversible Denaturation of Enzymes by Sodium Dodecyl Sulfate," J. Biol. Chem., 246(14): 4504–4509 (Jul. 25, 1971).

Fox et al, "SDS Removal from Protein by Polystyrene Beads", Analytical Biochem., 87:253–256 (Jun. 1978).

D. Hager and R. R. Burgess, "Elution of Proteins from Sodium Dodecyl Sulfate–Polyacrylamide Gels, Removal of Sodium Dodecyl Sulfate, and Renaturation of Enzymatic Activity: Results with Sigma Subunit of Escherichia coli RNA Polymerase, Wheat Germ DNA Topoisomerase, and Other Enzymes," Analytical Biochem., 109:76–86 (Nov. 1980).

L. T. Lee et al. "Removal of Unbound Sodium Dodecyl Sulfate (SDS) From Proteins in Solution by Electrophoresis Through Titon X–100–Agarose," J. Immunol. Meth., 19:69–75 (Jan. 1978).

W. J. Jankowski et al, "Binding of Human Interferons to Immobilized Cibacron Blue F3GA: The Nature of Molecular Interaction," Biochem., 15:(23):5182–5187 (Nov. 17, 1976).

K. Berg et al, "Affinity Chromatography of Human Leukocyte and Diploid Cell Interferons On Sepharose–Bound Antibodies," J. Immunol., 114(2):640–644 (Part I, Feb. 1975).

K. Berg et al, "Sequential Antibody Affinity Chromatography of Human Leukocyte Interferon," Scand. J. Immunol., 6:77–86 (Jan. 1977).

K. Berg and I. Heron, "The Complete Purification of Human (List continued on next page.)

Primary Examiner—Chhaya D. Sayala
Attorney, Agent, or Firm—Howson and Howson

[57] ABSTRACT

This invention provides a novel improved alpha interferon composition characterized by high specific activity, a purity of greater than 95% and which upon use in humans is further characterized by a substantial reduction in side effects normally associated with alpha interferon compositions. Also provided is a method for large scale production of the composition from human peripheral blood leukocytes. This alpha interferon composition may be used therapeutically in the treatment of cancers and diseases of the immune system and/or viral etiology.

10 Claims, 9 Drawing Sheets

OTHER PUBLICATIONS

Leukocyte Interferon," *Scand. J. Immunol.*, 11:489–502 (Apr. 1980).

J. De Maeyer–Guignard et al, "Purification of Mouse Interferon By Sequential Affinity Chromatography on Poly (U)— and Antibody–Agarose Columns," *Nature*, 271:622–625 (Feb. 16, 1978).

K. Berg et al, "Purification of Humans Interferons by Antibody Affinity Chromatography," *Texas Rept. on Biol. and Med.* 35:187–192 (1977).

K. Berg et al, "Pure Human Leukocyte Interferon," Proc. from Second Internat'l Workshop at Sloan–Kettering Instit. in New York (Apr. 22–24 1979).

D. Goeddel et al, "The Structure of Eight Distinct Cloned Human Leukocyte Interferon cDNAs", *Nature*, 290:20–26 (Mar. 5, 1981).

D. Bowden et al, "Cloning of Eukaryotic Genes in Single–Strand Phage Vectors: the Human Interferon Genes", *Gene*, 27:87–99 (1984).

O. Ohara et al, "Anomalous Behavior of Human Leukocyte Interferon Subtypes on Polyacrylamide Gel Electrophoresis in the Presence of Dodecyl Sulfate", *FEBS Letters*, 211(1):78–82 (Jan. 1987).

A. Friedman–Kien et al, "Natural Interferon Alpha for Treatment of Condylomata Acuminata", *JAMA*, 259(4):533–538 (Jan. 22/29, 1988).

Physicians Desk Reference, 47th edit., eds. Medical Economics Data, Montvale, NJ, pp. 2194 and 2006 (1993).

M. Khan et al, "Inhibition of Growth, Transformation, and Expression of Human Papillomavirus Type 16 E7 in Human Keratinocytes by Alpha Interferons", *J. Virol.*, 67(6):3396–3403 (Jun. 1993).

S. Sperber et al, "Anti–HIV–1 Activity of Recombinant and Hybrid Species of Interferon–alpha", *J. Interferon Res.*, 12:363–368 (1992).

H. Hochkeppel et al, "Murine AIDS: Effect of a rHu Interferon Alpha–B/D Hybrid (IFN) Against Herpes Simplex Virus Superinfection", *J. Cellular Biochem.*, Suppl. 14D, UCLA Symposia on Molecular and Cellular Biology, Abstracts, 19th Annual Meetings, Mar. 11–Apr. 6, 1990, Abstract L319, p. 136.

J. Gangemi et al, "9–(2–Phosphonylmethoxyethyl) Adenine in the Treatment of Murine Acquired Immune Deficiency Disease and Opportunistic Herpes Simplex Virus Infections", *Antimicrobial Agents and Chemotherapy*, 33(11):1864–1868 (Nov. 1989).

H. Lane et al, "Interferon–alpha in Patients with Asymptomatic Human Immunodeficiency Virus (HIV) Infection", *Annals of Internal Medicine*, 112:805–811 (Jun. 1, 1990).

S. Pestka, "Interferons—Part A", *Meth. Enzymol.*, 78:22–23 (1981).

K. Zoon, "Purification and Characterization of Human Interferon from Lymphoblastoid (Namalva) Cultures", *Meth. Enzymol.*, 78:457–465 (1981).

M.–J. Liao et al, "Absence of Neutralizing Antibodies to Interferon in Condyloma Acuminata and Cancer Patients Treated with Natural Human Leukocyte Interferon", *J. Infect. Dis.*, 165:757–760 (1992).

T. Khavkin et al, "Interactions of Human Monoblastoid Cells (U937) with Sendai Virus and Induction of alpha–Interferon", *J. Leukocyte Biology*, 1992 Annual Meeting Abstracts, Suppl. 3, Abstract, 137:36 (1992).

M. Padhye et al, "Optimization of Interferon Production from Human Peripheral Blood Leukocytes", *Keynote Symposia in Growth Factors and Inhibitors*, (Jan. 26–Feb. 2, 1992).

G. Linette et al, "Inactivation of HIV–1 in Preparations of Human Interferon by Low pH Treatment", *Cancer Therapy and Control*, 1:109–120 (1990).

H. Axelrod et al., "Trace Amounts of Murine Immunoglobulin in Affinity Purified Leukocyte Interferon Alpha are not Immunogenic", *Biotechnology Ther.*, 3(1&2):35–49 (1992).

R. Wells et al, "Interferon–alphan1 in Children with Recurrent Acute Lymphocytic Leukemia: A Phase I Study of Pharmacokinetics and Tolerance", *J. Interferon Res.*, 8:309–318 (1988).

A. Billiau, "Interferon Therapy: Pharmacokinetic and Pharmacological Aspects", *Arch. Virol.*, 67:121–133 (1981).

G. Dusheiko et al, "Recombinant Leukocyte Interferon Treatment of Chronic Hepatitis B", *Hepatology*, 5(4):556–560 (1985).

P. Burman et al, "Thyroid Autoimmunity in Patients on Long Term Therapy with Leukocyte–Derived Interferon", *J. Clin. Endocrinology and Metabolism*, 63(5):1086–1090 (1986).

M. Talpaz et al, "Hematologic Remission and Cytogenic Improvement Induced by Recombinant Human Interferon Alpha in Chronic Myelogenous Leukemia", *New England J. Med.*, 314(17):1065–1069 (Apr. 24, 1986).

G. Scott et al, "Skin Reactions to Interferon Inoculations are Reduced but not Abolished by Purification", *J. Interferon Res.*, 1(1):79–85 (1980).

F. Barouki et al, "Time Course of Interferon Levels, Antiviral State, 2',5'–Oligoadenylate Synthetase and Side Effects in Healthy Men", *J. Interferon Res.*, 7:29–39 (1987).

R. Wills et al, "Interferon Kinetics and Adverse Reactions After Intravenous, Intramuscular, and Subcutaneous Injection", *Clin. Pharmacol. Ther.*, 35(5):722–727 (May 1984).

G. Jones et al, "Safety and Tolerance of Recombinant Interferon Alfa–2a (Roferon–A) in Cancer Patients", *Cancer*, 57:1709–1715 (Apr. 15 Suppl. 1986).

H.–G. Klingemann et al, "Treatment with Recombinant Interferon (alpha–2beta) Early After Bone Marrow Transplantation in Patients at High Risk for Relapse", *Blood*, 78(12):3306–3311 (Dec. 15, 1991).

R. Reichel et al, "Clinical Study with Recombinant Interferon Gamma Versus Interferon–Alpha–2c in Patients with Condylomata Acuminata", *J. STD & AIDS*, 3:350–354 (Sep./Oct. 1992).

T. Taguchi, "Clinical Studies of Recombinant Interferon Alfa–2a (Roferon–A) in Cancer Patients", *Cancer*, 57:1705–1708 (1986).

R. Speigel, "Clinical Overview of Alpha Interferon", *Cancer*, 59:626–631 (1987).

J. Gangemi et al, "Antiviral Activity of a Novel Recombinant Human Interferon/alphaB/D Hybrid", *J. Interferon Res.*, 9:227–237 (1989).

S. Pestka et al, "Interferons and Their Actions", *Ann. Rev. Biochem.*, 56:727–777 (1987).

S. Nagata et al, "Synthesis in *E. coli* of a Polypeptide with Human Leukocyte Interferon Activity", *Nature*, 284:316–320 (Mar. 27, 1980).

A. Mizrahi, "Production of Human Lymphoblastoid (Namalva) Interferon", *Meth. Enzymol.*, 78:54–68 (1981).

A. Phillips et al, "Large–Scale Production of Human Interferon from Lymphoblastoid Cells", *Meth. Enzymol.*, 119:35–38 (1986).

K. Mogensen et al, "Production and Preparation of Human Leukocyte Interferon", *Pharmacol. Ther. C*, 1:369–381 (1977).

K. Cantell et al, "Production of Interferon in Human Leukocytes from Normal Donors with the Use of Sendai Virus", *Methods Enzymol.*, 78:29–38 (1981).

B. Horowitz, "Large-Scale Production and Recovery of Human Leukocyte Interferon from Peripheral Blood Leukocytes", *Methods Enzymol.*, 119:39–47 (1986).

P. Weck et al, "Interferons in the Treatment of Genital Human Papillomarvirus Infections", *Am. J. Med.*, 85(Suppl 2A):159–164 (Aug. 29, 1988).

J. Korenman et al, "Long-Term Remission of Chronic Hepatitis B After Alpha-Interferon Therapy", *Annal. Intern. Med.*, (114(8):629–634 (Apr. 15, 1991).

S. Baron et al, "Special Communications—The Interferons—Mechanisms of Action and Clinical Applications", *JAMA*, 266(10):1375–1383 (Sep. 11, 1991).

M. Hirsch, "Antiviral Drug Development for the Treatment of Human Immunodeficiency Virus Infections (An Overview)", *Am. J. Med.*, 85(Supp 2A):182–185 (Aug. 29, 1988).

P. Weck et al, "Antiviral Activity of Bacteria-Derived Human Alpha Interferons Against Encephalomyocarditis Virus Infection of Mice", *Infect. Immun.*, 35(2):660–665 (Feb. 1982).

E.-D. Kreuser et al, "Modulation of Integrin Expression by Cytokines on Colon Cancer Cell Lines", *Onkologies*, 14(Suppl. 2), Abstract No. 270, pp. 92–93 (1991).

H. Harada et al, "Distinction of Two Subtypes of Human Leukocyte Interferon (IFN-alpha) on B Cell Activation, B Cell Proliferation of Two Subtypes of IFN-alpha", *J. Immunol.*, 131(1):238–243 (Jul. 1983).

D. Goeddel et al, "Human Leukocyte Interferon Produced by *E. coli* is Biologically Active", *Nature*, 287:411–416 (Oct. 2, 1980).

M. Streuli et al, "At Least Three Human Type Alpha Interferons: Structure of alpha2", *Science*, 209:1343–1347 (Sep. 19, 1980).

A. Lok et al, "Interferon Antibodies may Negate the Antiviral Effects of Recombinant alpha-Interferon Treatment in Patients with Chronic Hepatitis B Virus Infection", *Hepatology*, 12(6):1266–1270 (1990).

S. Jacobs et al, "Minimal Antigenicity of Intron A in Human Recipients Demonstrated by Three Analytical Methods", *J. Biol. Resp. Mod.*, 7:447–456 (1988).

P. Weck et al, "Detection and Incidence of Neutralizing Antibodies to Interferon-alpha-n1", *J. Interferon Res.*, 9(Suppl 1):S37– S43 (1989).

P. Von Wussow et al, "Clinical Significance of Anti-IFN-alpha Antibody Titres During Interferon Therapy", *Lancet*, 2:635–636 (Sep. 12, 1987).

K. Cantell et al, "partial Purification of Human Leukocyte Interferon on a Large Scale", *Meth. Enzymol.*, 78:449–512 (1981).

K. Berg et al, "Antibody Affinity Chromatography of Human Leukocyte Interferon", *Meth. Enzymol.*, 78:487–499 (1981).

H. Axelrod et al, "Assessment of Anti-Interferon Antibodies in Patients Receiving Immunoaffinity Purified Human Interferon Alpha (ALFERON)", *Future Development of Interferon*, Proceedings 1988 Annual Meeting of the Int'l. Society for Interferon Research, Post Sumiferon Symposium, Sumitomo Pharmaceuticals Co., Ltd., publ. (Nov. 19, 1988).

1a 1b   2 3 4 5   6

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Region
        ( B ) LOCATION: 2
        ( D ) OTHER INFORMATION: /note="this amino acid may be Cys"

( i x ) FEATURE:
        ( A ) NAME/KEY: Region
        ( B ) LOCATION: 10
        ( D ) OTHER INFORMATION: /note="this amino acid may be Thr"

( x i ) SEQUENCE DESCRIPTION: SEQ ID NO:1:

```
Ala  Xaa  Val  Ile  Gln  Gly  Val  Gly  Val  Xaa  Glu  Thr  Pro
 1              5                         10
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Region
        ( B ) LOCATION: 3
        ( D ) OTHER INFORMATION: /note="this amino acid may also be Arg"

( x i ) SEQUENCE DESCRIPTION: SEQ ID NO:2:

```
Leu  Arg  Ser  Lys  Glu
 1              5
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:3:

Leu Lys Ser Lys Glu
1               5

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

Leu Arg Ser Lys Glu
1               5

( 2 ) INFORMATION FOR SEQ ID NO:5:

( i ) SEQUENCE CHARACTERISTICS:
        ( A ) LENGTH: 34 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Region
        ( B ) LOCATION: 1
        ( D ) OTHER INFORMATION: /note="this amino acid may be Cys"

( i x ) FEATURE:
        ( A ) NAME/KEY: Region
        ( B ) LOCATION: 11
        ( D ) OTHER INFORMATION: /note="this amino acid may also be Ser"

( i x ) FEATURE:
        ( A ) NAME/KEY: Region
        ( B ) LOCATION: 14
        ( D ) OTHER INFORMATION: /note="this amino acid may also be Thr"

( i x ) FEATURE:
        ( A ) NAME/KEY: Region
        ( B ) LOCATION: 16
        ( D ) OTHER INFORMATION: /note="this amino acid may also be Met"

( i x ) FEATURE:
        ( A ) NAME/KEY: Region
        ( B ) LOCATION: 19
        ( D ) OTHER INFORMATION: /note="this amino acid may also be Gly"

( i x ) FEATURE:
        ( A ) NAME/KEY: Region
        ( B ) LOCATION: 22
        ( D ) OTHER INFORMATION: /note="this amino acid may also be Gly"

( i x ) FEATURE:
        ( A ) NAME/KEY: Region
        ( B ) LOCATION: 27
        ( D ) OTHER INFORMATION: /note="this amino acid may also be Pro"

( i x ) FEATURE:
        ( A ) NAME/KEY: Region
        ( B ) LOCATION: 29
        ( D ) OTHER INFORMATION: /note="this amino acid may be Cys"

(x i) SEQUENCE DESCRIPTION: SEQ ID NO:5:

```
Xaa Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Xaa Xaa Xaa Asp
            20                  25                  30

Arg His
```

(2) INFORMATION FOR SEQ ID NO:6:

(i) SEQUENCE CHARACTERISTICS:
        (A) LENGTH: 34 amino acids
        (B) TYPE: amino acid
        (C) STRANDEDNESS: unknown
        (D) TOPOLOGY: unknown (i i) MOLECULE TYPE: protein (x i) SEQUENCE DESCRIPTION: SEQ ID NO:6:

```
Xaa Asp Leu Pro Gln Thr His Ser Leu Gly Ser Arg Arg Thr Leu Met
1               5                   10                  15

Leu Leu Ala Gln Met Arg Arg Ile Ser Leu Pro Xaa Xaa Leu Xaa Asp
            20                  25                  30

Arg His
```

(2) INFORMATION FOR SEQ ID NO:7:

(i) SEQUENCE CHARACTERISTICS:
        (A) LENGTH: 34 amino acids
        (B) TYPE: amino acid
        (C) STRANDEDNESS: unknown
        (D) TOPOLOGY: unknown (i i) MOLECULE TYPE: protein (x i) SEQUENCE DESCRIPTION: SEQ ID NO:7:

```
Xaa Asp Leu Pro Gln Thr His Ser Leu Gly Ser Arg Arg Thr Leu Met
1               5                   10                  15

Leu Leu Ala Gln Met Arg Arg Ile Xaa Leu Pro Ser Xaa Leu Lys Asp
            20                  25                  30

Arg His
```

(2) INFORMATION FOR SEQ ID NO:8:

(i) SEQUENCE CHARACTERISTICS:
        (A) LENGTH: 34 amino acids
        (B) TYPE: amino acid
        (C) STRANDEDNESS: unknown
        (D) TOPOLOGY: unknown (i i) MOLECULE TYPE: protein (i x) FEATURE:
        (A) NAME/KEY: Region
        (B) LOCATION: 11
        (D) OTHER INFORMATION: /note="this amino acid may also be
            Ser"

(i x) FEATURE:
        (A) NAME/KEY: Region
        (B) LOCATION: 22
        (D) OTHER INFORMATION: /note="this amino acid may also be
            Arg"

(x i) SEQUENCE DESCRIPTION: SEQ ID NO:8:

```
Xaa Asp Leu Pro Gln Thr His Ser Leu Gly Asn Arg Arg Ala Leu Ile
1               5                   10                  15
```

```
          Leu  Leu  Ala  Gln  Met  Gly  Arg  Ile  Ser  His  Phe  Ser  Xaa  Leu  Xaa  Asp
                         20                      25                      30

Arg  His
```

( 2 ) INFORMATION FOR SEQ ID NO:9:

( i ) SEQUENCE CHARACTERISTICS:
      ( A ) LENGTH: 34 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:9:

```
Xaa  Asp  Leu  Pro  Gln  Thr  His  Ser  Leu  Gly  Asn  Arg  Arg  Ala  Leu  Ile
 1                   5                        10                      15

Leu  Leu  Gly  Gln  Met  Gly  Arg  Xaa  Xaa  Xaa  Xaa  Xaa  Xaa  Xaa  Xaa  Xaa
               20                      25                      30

Xaa  Xaa
```

( 2 ) INFORMATION FOR SEQ ID NO:10:

( i ) SEQUENCE CHARACTERISTICS:
      ( A ) LENGTH: 34 amino acids
      ( B ) TYPE: amino acid
      ( C ) STRANDEDNESS: unknown
      ( D ) TOPOLOGY: unknown ( i i ) MOLECULE TYPE: protein ( i x ) FEATURE:
      ( A ) NAME/KEY: Region
      ( B ) LOCATION: 22
      ( D ) OTHER INFORMATION: /note="this amino acid may also be
            Gly"

( x i ) SEQUENCE DESCRIPTION: SEQ ID NO:10:

```
Xaa  Asp  Leu  Pro  Gln  Thr  His  Ser  Leu  Gly  Asn  Arg  Arg  Ala  Leu  Ile
 1                   5                        10                      15

Leu  Leu  Ala  Gln  Met  Arg  Arg  Ile  Ser  Pro  Phe  Ser  Xaa  Leu  Lys  Asp
               20                      25                      30

Arg  His
```

( 2 ) INFORMATION FOR SEQ ID NO:11:

( i ) SEQUENCE CHARACTERISTICS:
      ( A ) LENGTH: 34 amino acids
      ( B ) TYPE: amino acid
      ( C ) STRANDEDNESS: unknown
      ( D ) TOPOLOGY: unknown ( i i ) MOLECULE TYPE: protein ( i x ) FEATURE:
      ( A ) NAME/KEY: Region
      ( B ) LOCATION: 10
      ( D ) OTHER INFORMATION: /note="this amino acid may also be
            Arg"

( x i ) SEQUENCE DESCRIPTION: SEQ ID NO:11:

```
Xaa  Asp  Leu  Pro  Gln  Thr  His  Ser  Leu  Gly  Asn  Arg  Arg  Ala  Leu  Ile
 1                   5                        10                      15

Leu  Leu  Ala  Gln  Met  Gly  Arg  Ile  Ser  Pro  Phe  Ser  Xaa  Leu  Xaa  Asp
               20                      25                      30

Arg  His
```

( 2 ) INFORMATION FOR SEQ ID NO:12:

( i ) SEQUENCE CHARACTERISTICS:
        ( A ) LENGTH: 34 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:12:

```
Xaa Asp Leu Pro Gln Thr His Ser Leu Gly Asn Arg Arg Ala Leu Ile
 1               5                  10                      15

Leu Leu Ala Xaa Met Arg Arg Ile Ser Pro Phe Ser Xaa Leu Lys Asp
            20                  25              30

Arg His
```

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:13:

```
Leu Arg Arg Lys Asp
 1               5
```

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:14:

```
Leu Arg Ser Lys Glu
 1               5
```

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:15:

```
Leu Lys Ser Lys Glu
 1               5
```

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:16:

Leu Arg Arg Lys Asp
1               5

( 2 ) INFORMATION FOR SEQ ID NO:17:

( i ) SEQUENCE CHARACTERISTICS:
      ( A ) LENGTH: 5 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:17:

Leu Arg Arg Lys Asp
1               5

( 2 ) INFORMATION FOR SEQ ID NO:18:

( i ) SEQUENCE CHARACTERISTICS:
      ( A ) LENGTH: 5 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:18:

Leu Arg Arg Lys Glu
1               5

( 2 ) INFORMATION FOR SEQ ID NO:19:

( i ) SEQUENCE CHARACTERISTICS:
      ( A ) LENGTH: 5 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:19:

Leu Arg Arg Lys Asp
1               5

( 2 ) INFORMATION FOR SEQ ID NO:20:

( i ) SEQUENCE CHARACTERISTICS:
      ( A ) LENGTH: 5 amino acids
      ( B ) TYPE: amino acid
      ( C ) STRANDEDNESS: unknown
      ( D ) TOPOLOGY: unknown ( i i ) MOLECULE TYPE: protein ( i x ) FEATURE:
      ( A ) NAME/KEY: Region
      ( B ) LOCATION: 3
      ( D ) OTHER INFORMATION: /note="this amino acid may also be
            Arg"

( x i ) SEQUENCE DESCRIPTION: SEQ ID NO:20:

Leu Arg Ser Lys Glu
1               5

( 2 ) INFORMATION FOR SEQ ID NO:21:

( i ) SEQUENCE CHARACTERISTICS:

( A ) LENGTH: 5 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:21:

Leu  Arg  Ser  Lys  Glu
1                      5

( 2 ) INFORMATION FOR SEQ ID NO:22:

( i ) SEQUENCE CHARACTERISTICS:
( A ) LENGTH: 5 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:22:

Leu  Arg  Ser  Lys  Glu
1                      5

ALPHA INTERFERON COMPOSITION AND METHOD FOR ITS PRODUCTION FROM HUMAN PERIPHERAL BLOOD LEUKOCYTES

CROSS-REFERENCE TO OTHER APPLICATIONS

This is a 371 of PCT/U.S.93/01135 and a continuation-in-part of U.S. patent application Ser. No. 835,030, filed Feb. 10, 1992 now abandoned.

FIELD OF THE INVENTION

This invention relates generally to alpha interferon compositions. More specifically, the invention relates to an improved alpha interferon composition characterized by high specific activity, a purity of greater than 95% and which upon use in humans is further characterized by a substantial reduction in side effects normally associated with alpha interferon compositions, and a method for large scale production of the composition from human peripheral blood leukocytes.

BACKGROUND OF THE INVENTION

Human alpha interferon comprises a family of more than fifteen proteins with antiviral, antigrowth and immunoregulatory activities [Pestka et al., *Ann. Rev. Biochem.*, 56:727 (1987)]. The therapeutic efficacy of human alpha interferons has been established for human cancers and viral diseases. For example, recombinant interferons (IFN alfa-2a, IFN alfa-2b, IFN alfa-2c), cell-line derived interferon (IFN alfa-n1) and interferon derived from leukocytes (IFN alfa-n3) are currently used for the treatment of *Condyloma acuminata*, hepatitis [Weck et al., *Am. J. Med.*, 85(Suppl 2A):159 (1988); Korenman et al., *Annal. Intern. Med.*, 114.:629 (1991); Friedman-Kien et al., *JAMA*, 259:533 (1988)], for the regression of some malignancies [Baron et al., *JAMA*, 266:1375 (1991)], for the treatment of AIDS related Kaposi's sarcoma [Physicians Desk Reference, 47th edit., eds. Medical Economics Data, Montvale, N.J., p. 2194 and 2006 (1993)] and are currently being considered for the treatment of human acquired immunodeficiency syndrome (AIDS) either alone or in combination with other antiviral agents [Hirsch, *Am. J. Med.*, 85(Suppl 2A):182 (1988)].

Recombinant interferons can be made by using genetic engineering techniques, for example, in Escherichia coli in large scale [Goeddel et al., *Nature*, 287:411 (1980); Streuli et al., *Science*, 209:1343 (1980)]. However, genetically engineered interferons are composed of only a single species, which is not post-translationally modified at all or identically to the natural interferons, and which may limit the biological activity of the composition. For example, IFN-α2 is the sole species in the products Intron® A (IFN alfa-2b) [Schering Plough] and Roferon® A (IFN alfa-2a) [Hoffman-La Roche].

Interferons derived from natural sources, such as those from human lymphoblastoid, Namalwa, cell line [Mizrahi, *Meth. Enzymol.*, 78:54 (1981); Phillips et al., *Meth. Enzymol.*, 119:35 (1986)], and those from human peripheral blood leukocytes [Mogensen et al., *Pharmacol. Ther. Part C*, 1:369 (1977); Cantell et al., *Methods Enzymol.*, 78:29 (1981); Horowitz, *Methods Enzymol.*, 119:39 (1986)], are composed of multiple species, each with different structural and biological activity.

Such "natural" interferons are considered by some researchers to provide potentially better therapeutic efficacy than recombinant interferon. For example, natural alpha interferon can be used at a four times lower dosage to treat *Condyloma* than the recombinant products [see, e.g., Physicians Desk Reference, cited above, at pages 1879 and 2194]. The most significant advantage of using natural leukocyte interferon as a therapeutic agent has been its low immunogenecity in patients receiving interferon treatment. It has been documented that patients treated with the recombinant interferons identified above, and lymphoblastoid interferon Wellferon® IFN alfa-n1 [Burroughs Wellcome] have developed neutralizing antibodies to interferon [Lok et al., *Hepatology*, 12:1266 (1990); Jacobs et al., *J. Biol. Resp. Mod.*, 7:447 (1988); Weck et al., *J. Interferon Res.*, 1(Suppl):S37 (1989)]. However, patients treated with leukocyte derived interferon (IFN alfa-n3 or Cantell's partially purified interferon preparation) do not generate detectable serum antibody to interferon [Von Wussow et al., *Lancet*, 2:635 (1987); Liao et al., *J. Infect. Dis.*, 165:757–760 (1992)]. The presence of neutralizing anti-interferon antibodies may potentially block the therapeutic effect of the interferon and therefore may be a significant factor in the course of clinical treatment. However, many of such patients resistant to recombinant alpha interferon have been shown to respond to natural alpha interferon treatment.

Previously reported methods for alpha interferon production from human peripheral blood leukocytes are both inefficient and very costly [Mogensen et al., (1977); Cantell et al., (1981); and Horowitz, (1986), all cited above]. Cantell's published method of producing natural alpha interferon from leukocytes results in the generation of a relatively low titer of interferon (60,000 CPE U/ml) from a relatively high cell density ($1 \times 10^7$ cells/ml).

Prior methods of purification of natural alpha interferon also have their limitations. For example, Cantell et al., *Meth. Enzymol.*, 78:499 (1981) describes only the partial purification of human leukocyte interferon on a large scale using sequential precipitation method. The resultant interferon is approximately 1% pure containing multiple interferon species. Berg et al., *Meth. Enzymol.*, 78:487 (1981) describe Sepharose 4B-conjugated monoclonal antibody affinity chromatography for purification of human leukocyte interferon. Finally, Horowitz, (1986), cited above, describes large scale production and purification of human leukocyte interferon from peripheral blood leukocytes. He used either Cantell's precipitation method or NK2 antibody affinity chromatography.

There are increasing numbers of alpha interferon preparations now being used in patients and in clinical trials for various indications. However, all have been characterized by a number of side effects in patients. Such flu-like symptoms include fever, low blood cell counts, gastrointestinal disorders, such as vomiting and diarrhea, renal disorders, pulmonary disorders, allergic reactions, such as bronchospasm or anaphylaxis or skin rashes, hair loss, and infection, which are identified in the product literature for alpha interferons now on the market.

While some of the side effects are minor, they can have serious negative impacts on patients who must take significant doses of the compositions for long periods of time. For example, for certain therapies, e.g., the treatment of AIDS-related Kaposi's sarcoma and a symptomatic AIDS, the dosage at which the interferons are effective produces side effects which are worse than the effects of the disease at certain stages. In clinical trials for these indications, the occurence of the side effects has resulted in patients abandoning the procedure despite its probable long term benefit [H C. Lane et al, *Annals of Internal Medicine*, 112:805 (1990)].

Thus, there remains a need for an improved alpha interferon composition which can be characterized by very low toxicity and high purity and which can produce minimal side effects in patients undergoing interferon therapy.

SUMMARY OF INVENTION

In one aspect, the present invention provides a substantially pure alpha interferon composition comprising a natural mixture of human alpha interferon species or subspecies. This composition is further characterized by a very high specific activity of about $4 \times 10^8$ U/mg. Significantly, this composition is characterized by the ability to produce therapeutic effects in human patients with a substantial reduction in side effects normally associated with alpha interferons.

In another aspect, the invention provides pharmaceutical compositions comprising as one active ingredient, an effective amount of the alpha interferon composition of the invention in a pharmaceutically acceptable carrier. The pharmaceutical composition may contain the alpha interferon composition in combination with any other conventional pharmaceutical agent useful in the treatment of selected diseases or disorders.

In still another aspect, the present invention provides a novel method of producing the alpha interferon composition described above from human peripheral blood leukocytes, the method characterized by several optimized steps for induction and purification which permit the efficient and cost effective production of large quantities of the composition.

In yet another aspect, this invention is directed to the use of the purified alpha interferon composition of this invention in the treatment of various diseases or disorders of the immune system, cancer and/or viral diseases. These methods for treatment comprise administering the pharmaceutical compositions of the invention, either alone or in conjunction with other drugs, to a human patient.

Other aspects and advantages of the present invention are described further in the following detailed description of preferred embodiments of the present invention.

DETAILED DESCRIPTION OF THE INVENTION

Figure 1:
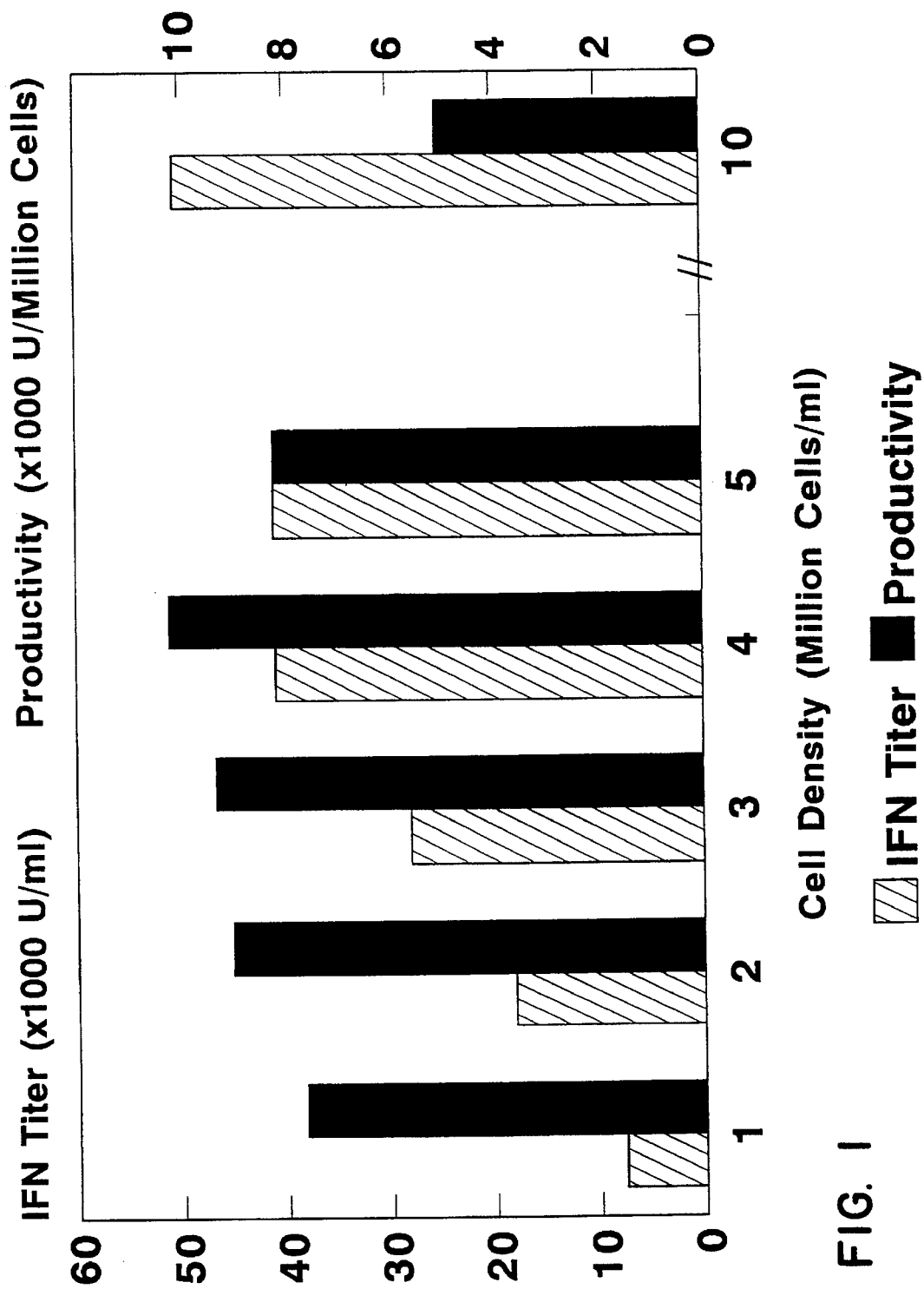
FIG. 1 illustrates interferon titer and leukocyte productivity as a function of cell density. Productivity is determined as interferon IRMA units per $10^6$ leukocytes.
Figure 2:
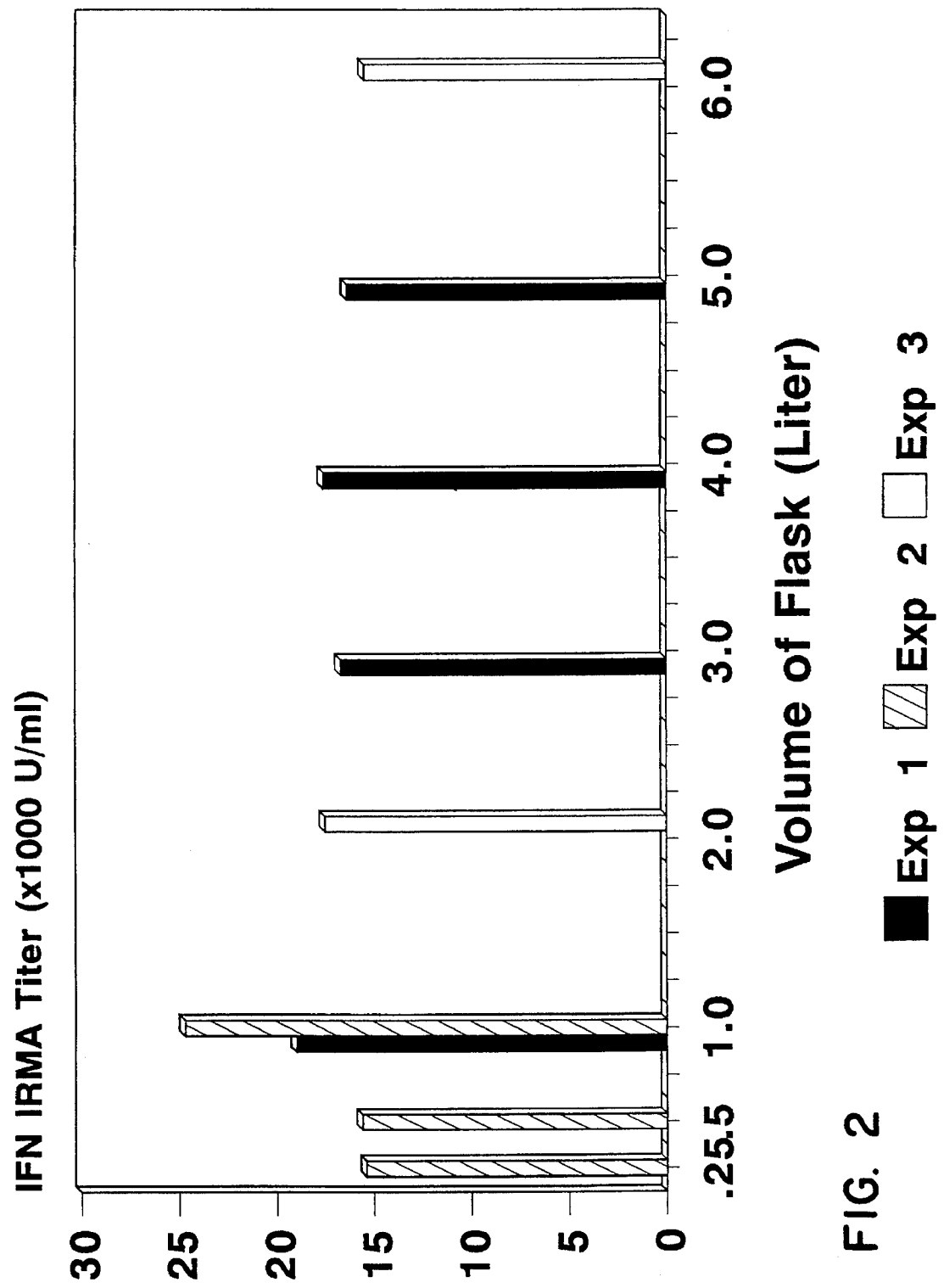
FIG. 2 illustrates interferon titer as a function of induction culture volume in a 6-liter flat-bottom flasks.

The present invention provides an improved alpha interferon composition, referred to herein for simplicity as IFN α-n3a, a method for producing the composition, and pharmaceutical compositions containing the IFN α-n3a composition for therapeutically treating diseases susceptible to treatment with alpha interferon.

1. The Composition

The alpha interferon composition of this invention is a purified mixture of natural human alpha interferon species and subunits. As described in detail below, this composition of the present invention differs from another natural alpha interferon product, i.e., IFN alfa-n3, by having greater than two times higher antiviral specific activity, at least five times less impurities, and at least five times less pyrogen activity.

The IFN α-n3a protein population contains proteins defined by their amino acid sequences that can be identified by the interferon gene sequences reported in the literature. Specifically, the IFN α-n3a composition comprises a mixture of at least six human alpha interferon protein species. Based on the N-terminal sequencing described below, at least one alpha interferon species is selected from α2b, α2c, or a combination of both species. At least a second species is selected from one or a combination of α4a, α4b, and/or α16. Still a third of the six species is selected from one or a combination of α7a, α7b, and/or α7c. A fourth of the species is selected from one or a combination of α8a, α8b, and/or α8c. A fifth species in the mixture is α10a. Finally a sixth species of alpha interferons in the mixture is one or a combination of α17a, α17b, α17c, α17d, α21a and/or α21b. The sequences of all of these interferon species are available on a variety of commercial databases, including the Genbank® database [Intell Genetics, Inc., Mountain View, Calif.]. The mixture of proteins in IFN α-n3a does not contain IFN-α14, IFN-α2a nor IFN-α1 species.

The above-identified species or subspecies of alpha interferon present in the composition have been characterized using reverse-phase high performance liquid chromatography (RP-HPLC) to separate interferon species according to their relative hydrophobicity as described in detail in Example 3. The IFN α-n3a composition has a hydrophobicity, measured on a RP-HPLC column, eluting between 40–60% acetonitrile. Both N-terminal and C-terminal sequences for the above-identified alpha interferon species or subspecies have been identified in this composition, as described in detail in Example 6, parts B and D.

The IFN α-n3a composition of the invention is also characterized by its activity in several biological assays. As described in detail in Example 4A, an antiviral assay [see, e.g., Linnette et al, *Cancer Therapy and Control*, 1:109–120 (1990)] was performed on human, bovine and rabbit cells. The antiviral specific activity of IFN α-n3a on human and bovine cells in the assay ranges from $1-10 \times 10^8$ U/mg and is generally $\geq 2 \times 10^8$ U/mg. The interferon unit in this assay is defined as the reciprocal of the dilution at the 50% endpoint and is adjusted to the NIH reference standard (International Leukocyte Interferon Reference Preparation, Ga 23-902-530). The average antiviral specific activity on human HEp-2 cells is about $4\times10^8$ U/mg.

It has been demonstrated that the species IFN-α2, represented by subspecies α2b and α2c, is present in the peaks 1a and 1b, and constitutes about 50% of the total IFN α-n3a protein mass, but is responsible for only about 25% of the total antiviral activity of the composition when these peaks are measured separately in this assay (see Table 4). Further, as described in detail in Example 8, IFN α-n3a is 10 to 100-times more potent than equal concentrations of recombinant interferon α2 for in vitro antiviral activity against HIV in monocytes.

Biological activity was also measured in an antiproliferative assay on human cells, as described in Example 4B below [see, e.g., Gillis et al, *J. Immunol.*, 12:2027 (1978)]. The specific activity ranges from $1-10\times10^8$ U/mg, and generally $\geq 1\times10^8$ U/mg. The average antiproliferative specific activity on human Daudi cells is about $1.5\times10^8$ U/mg. The interferon unit in this assay is defined as the reciprocal of the dilution at 50% endpoint.

The bioactivity ($\geq 99\%$) of the composition, as determined in the antiviral assay, can be neutralized by a sheep polyclonal antiserum (raised to purified IFN alfa-n3) specific to human leukocyte interferons in a standard neutralization assay [Y. Kawade, *Meth. Enzymology*, 119:558–573 (1986)].

Additionally, in a rabbit pyrogen test [Pyrogen Test, USP XXII/NF XVII, United States Pharmacopeial Convention, Inc. p. 1515 (1990)], an increase in the average rabbit body temperature of about 0.2° C. is indicative of very low pyrogen in the composition. In fact, such a result is at least five times lower than the results for IFN alfa-n3.

The physical properties of the IFN α-n3a composition of this invention have also been determined. For example, this composition is substantially pure; that is, it is composed of greater than about 95% human alpha interferon proteins. Less than 5% of this composition contains contaminants such as non-human alpha interferon proteins, other nucleic acids or enzymes, lipids, and the like. More specifically, this composition is $\geq 98\%$ pure human alpha interferon proteins. Most preferably, it is about 99% pure human alpha interferon proteins.

The purity of the composition is measured both by sodium dodecylsulfate polyacrylamide gel electrophoresis (SDS-PAGE) and by Western blot procedures, as discussed in detail in Example 5 below. With reference to the method of production described below, this purification translates into an about 8000 fold purification from the first step NK2 affinity purification, and about 2 fold from the second step Superose purification. Total purification of IFN α-n3a is about 12,000 fold from the crude materials induced from the leukocytes, as described in detail below.

Western blot analyses (FIGS. 8 and 9) of the composition under non-reducing and reducing conditions, respectively, demonstrate that all protein bands are identified as human interferons with an impurity level in unfractionated interferon of about 1% or less. Subsequent fractionation on RP-HPLC, shows no detectable impurity in any of the peaks.

Two-dimensional gel analyses for unfractionated IFN α-n3a indicates that there are multiple spots detected for all samples, all recognized by LIT-1 monoclonal antibody (see Example 5, part A, below) indicating that they are interferon proteins. The apparent molecular weight of the composition ranges between 16 to 27 kilodaltons as measured on SDS-PAGE gels. The composition is also characterized by an isoelectric point ranging between 5.0 to 7.5, and more preferably between 5.5 and 6.5. The number of spots and molecular weights for proteins in each of the peaks are summarized in Example 5, in Table 8 below.

The biochemical properties of the interferon composition of this invention, e.g., determined by amino acid analyses, and amino and carboxyl terminal sequencing are described in detail in Example 6. The amino and carboxyl terminal sequencing indicates that the interferon composition contains intact interferon molecules, which consist of about 165–166 amino acid residues per molecule. The composition also contains two disulfide bonds.

The product was also characterized to determine content of carbohydrates, e.g., amino sugars, neutral sugars and sialic acids. This is also described in detail in Example 6C. The composition is characterized by O-linked carbohydrate glycosylation, with a carbohydrate composition consisting of galactosamine (GalN), glucosamine (GlcN), galactose, glucose, mannose, and sialic acid. On the average, the composition contains $\leq 6$ mole sugars/moles of interferon protein, and an average of between 1–3 mole sugar/mole interferon. The glycosylation of IFN α-n3a must be at a site other than the Asn residue responsible for the N-linked glycosylation, because IFN α-n3a does not contain IFN-α14, the only alpha interferon species reportedly with potential N-glycosylation at the Asn residue. The site for O-linked glycosylation has been determined by enzyme digestion followed by amino acid sequencing. Results show that threonine at position 106 is the site of glycosylation (Example 6C).

Other biochemical characteristics of the IFN α-n3a composition of this invention include the presence of binding sites for the monoclonal antibody, NK2 [Celltech, U.K.]. NK2 reportedly recognizes only a sub-group of alpha interferon species, i.e. α2(a/b/c), α8(a/b/c), α10a, α17(a/b/c/d), α7(a/b/c), α6 and α21(a/b). It does not recognize interferon species α1, α5, α10b, α14 or α-omega 1. The IFN α-n3a composition also has a pH stability at between about 2 and 9. The composition has a thermal stability at 56° C. for $\geq 2$ hours.

The alpha interferon compositions, IFN α-n3a, of the present invention differs significantly from other alpha interferons, both recombinant and natural, which are now being sold commercially or used in clinical trials. The most striking difference is the exceedingly low toxicity of IFN α-n3a, compared to the known alpha interferon compositions. In commercial brochures and literature describing IFN alfa-n3, that natural PBL-derived alpha interferon product produced typical alpha interferon side effects in a large percentage of patients tested.

Other differences also exist between the product of this invention and the prior art natural alpha interferon as demonstrated above. In comparison to the previous IFN alfa-n3 product used in clinical studies, the present composition IFN α-n3a has a 2-fold higher specific activity in the antiviral assay of about $4\times10^8$ U/mg. The present composition has at most about 2% impurities vs. the previous product's impurity level of between 5–10%. Additionally, the present composition has a very low pyrogen test result, e.g., about 0.2° C. vs. the result of previous IFN alfa-n3 of about 1° C. Differences also exist in the methods of preparation of the two products.

The differences in toxicity between the present invention and recombinant interferons are even more striking. In addition to the fact that this composition consists of a mixture of alpha interferon species vs. the single species in the recombinant products, natural alpha interferon is not made in bacteria, like the recombinant interferons, and therefore has no contaminating bacterial by-products likely to induce side effects in humans.

With regard to the reduction in side effects evidenced by the composition of this invention, Example 7 details the results of toxicity studies performed on the composition of the present invention according to procedures conventionally employed by the World Health Organization and described in W. B. Abrams et al, in "The Clinical Research Process in the Pharmaceutical Industry", G. M. Matoren, ed., Marcel Dekkev, Inc., chap 10, pp. 195–216 (1984). The toxicity studies performed on patients given the composition of the present invention demonstrated almost no side effects.

In fact, Table 16 below compares the side effects reported for other alpha interferon products known to the art to the side effects produced in the clinical studies of the composition of the present invention. This data demonstrates that the composition of this invention causes signficantly reduced side effects, resulting in a major advantage for the administration of the composition for long periods to patients. Additionally higher dosages of this composition may be administered to patients with reduced side effects compared to known alpha interferon products.

It is presently unknown to the inventors precisely why the composition of the present invention shows such a surprising degree of reduction of side effects. While not wishing to be bound by theory, the inventors believe that the reasons for the substantial reduction in toxicity and side effects, and resulting enhanced therapeutic efficacy of this composition may be based on the fact that the various human alpha interferon species present in this mixture are binding to more than one epitope or receptor in the cells of the patient being administered this composition. Further the very low amount of contaminants that are present in this composition may also be involved in the surprising characteristics of this composition.

Further, because the specific activity in antiviral and anti-proliferative assays is higher than that known for other alpha interferons, a smaller dosage may be administered to patients, which small dosage is likely to be lower than the toxic dosage of the composition, if any.

Additionally, the post-translational glycosylation of the proteins in this composition may contribute to a lack of aggregation, resulting in less side effects. The processing may result in less oxidated or less chemically modified amino acid residues on the alpha interferon proteins. The carbohydrate in alpha interferon proteins may be properly preserved during the process of producing this composition and thus similar to the natural alpha interferon proteins in the human body. The process may also result in mainly active alpha interferon monomers and little formation of inactive alpha interferon oligomers or protein aggregates.

2. The Method of Producing the Composition

In summary, the method for producing the alpha interferon composition of the present invention involves both an induction process and a purification process. The induction process is described in detail in Example 1 below, and the purification process is described in Example 2 below.

a. Induction

In the induction process, IFN α-n3a is produced by inducing human PBL suspensions with Sendai virus. The major factors which significantly affect the amount of leukocyte alpha interferon, IFN α-n3a, produced from peripheral blood leukocytes (PBLs) are: the density of cells during induction, the concentration of sodium bicarbonate in the induction medium, the concentration of human agamma serum, the concentration and type of primer, the kinetics of induction, the volume of the cultures in flasks, the stirring speed of the cultures, the temperature of induction, the composition of the media, and the concentration and characteristics of the Sendai virus.

According to this induction process, blood is drawn from healthy human donors and human PBLs are prepared by collecting buffy coats and lysing red blood cells with ammonium chloride, preferably 0.83% ammonium chloride. Then, the leukocytes are suspended in an induction medium at a desired cell density.

Cell densities can range from about $1-10\times10^6$ cells/ml. The relative efficiency of alpha interferon production can be determined by the amount of alpha interferon produced per cell in any specific cell density. The inventors determined that while the amount of alpha interferon produced generally increases proportionally with increasing concentration of cells, the optimal productivity of alpha interferon from human leukocytes is obtained at a cell density of $4\times10^6$ cells/ml. This productivity can be measured by the Immunoradiometric Assay (IRMA) [Celltech Ltd.], or in a cytopathic effect (CPE) assay described below. In these assays, the titers are reported as IRMA units/ml or, for the CPE assay, as IU/ml (international units/ml) as compared with a standard, as described below. While the maximum interferon titer (about 50,000 IRMA units/ml, equivalent to about 100,000 CPE units/ml) is observed when $1\times10^7$ leukocytes/ml are used during induction, the highest interferon productivity (about 43,000 IRMA units/ml, equivalent to about 86,000 CPE U/ml) is obtained at $4\times10^6$ cells/ml. Thus, the productivity of cells at a density of $10^7$ cell/ml is about half that found at $4\times10^6$ cells/ml. See, e.g., FIG. 1.

The induction medium is a minimum essential medium (MEM) desirably at a strength of between 0.5X to 1.5X, and containing Earle's salt, pH 7.4, supplemented with L-glutamine, non-essential amino acids, 4.46 mg/ml Tricine, and 24 µg/ml Neomycin sulfate. Current data suggests that the induction titer is the highest at 0.85X to 1.15X MEM concentration, which has an osmolarity close to physiological conditions.

It is also required for the induction medium to contain human IgG virtually depleted serum (agamma serum) for alpha interferon production. An effective serum concentration for interferon production is in the range of 0.1 to about 1.5 mg/ml, and more preferably 0.1 to about 1.0 mg/ml. Preferably a concentration of about 0.4 mg/ml is used.

Higher serum concentrations are not beneficial to the interferon production, possibly due to the presence of inhibitory factors in the serum preparations. The optimal serum concentration found in this production process is much lower than the recommended concentration of 2.4 mg/ml by Cantell's method. The use of lower serum concentration in the induction can significantly reduce the contribution of contaminating of serum proteins in the downstream processes for purification of interferons.

The induction process is optimized by the inclusion of several other components in the medium. Desirably the induction medium contains a high concentration of sodium bicarbonate ($NaHCO_3$), as opposed to methods of the prior art which employ no or low sodium bicarbonate. Increase of the concentration of sodium bicarbonate in MEM has significant effect (i.e., a 3 to 4 fold increase) on the yield of interferon produced. Preferred bicarbonate concentrations range between about 0.3 to about 2.5 mg/ml. More preferably, the range is from about 1.7 to 2.2 mg/ml. A concentration of 2.2 mg/ml sodium bicarbonate at least doubles the interferon titer produced according to the present invention.

One of the rate-limiting factors during interferon synthesis from PBLs may be an essential nutritional factor, such as rare minerals, vitamins or fatty acids. The addition of certain vitamins in the induction cultures in the present invention acts to increase interferon production. The addition of vitamin C and vitamin $B_3$ (niacin), individually, to the induction culture increases interferon yield by 20–30% compared to cultures without either of these vitamins. The effective concentrations of vitamin C for enhancing interferon production are between about 0.0002 to about 2 mg/ml. Vitamin C at higher concentrations than 2 mg/ml inhibits interferon production from PBLs. The effective concentrations of vitamin $B_3$ for enhancing interferon production are between about 0.5 to about 1000 µg/ml. Other compounds such as, ferrous sulfate, butyric acid, tocopherol phosphate, tocopherol, glucose, and cholesterol, have been found to either have no effect or be inhibitory on alpha interferon production.

The present invention provides a method for production of interferon in a wide range of volumes. The induction volume per flask may vary from 150 ml to 6 liters or higher. The volume of induction culture may be increased to full capacity (or decreased) as desired in induction flasks without affecting the interferon yield. In addition, because the flasks may be completely filled, the method of this invention allows scale up of interferon production with a minimal number of flasks, thus reducing the space and cost of interferon production. Large scale induction up to thousands of liters can be achieved by using multiple large flasks or bioreactors under similar induction conditions described in the present invention.

Crude or purified leukocyte alpha interferon is then added as a primer to the PBLs suspended in the induction medium. Both crude and purified natural leukocyte alpha interferon induced similar amounts of interferon from white blood cells when used as primers. The leukocytes may be primed with between 1 to about 100,000 international units (IU)/ml, and preferably about 10–100 IU/ml of the crude alpha interferon supernatant or purified alpha interferon. By "crude interferon" is meant the unpurified product resulting from the induction method described herein. By "purified interferon" is meant the IFN α-n3a resulting from both the induction and purification methods described herein.

It is anticipated that other interferons may be used as primers, e.g., IFN-beta, IFN-gamma and possibly other cytokines. For example, natural human IFN-gamma at concentrations of 100 to 1,000 IU/ml can stimulate alpha interferon production, but results in a lower increase in alpha interferon synthesis than that observed when either crude or purified natural alpha interferons are used as primers.

Optimal priming time was found to be approximately 2 to 3 hours prior to the addition of Sendai virus at about 36° C. Varying the priming time can result in significant changes in the amount of interferon secreted from leukocytes. Priming leukocytes for shorter than 1 hour results in a reduction of interferon yield. Priming for longer than 3 hours may not result in any appreciable gain. Preferably, in the priming step, leukocytes at $10^7$ cells/ml are primed with 20 IU/ml of crude interferon for about 3 hours.

After priming, Sendai virus, an important inducer of interferons, is added to the suspension of leukocytes. Interferon productivity can differ significantly in induction with different lots or preparations of the virus. The difference in interferon inducibility may be due to the presence of varying amounts of Sendai viral Defective Interfering (DI) particles in different virus preparations. High amounts of DI particles may have an inhibitory role in interferon production.

In general, adsorption of Sendai virus to leukocytes is most efficient at the high cell density described above with concentrated virus. The optimum virus concentration required for maximum interferon induction must be determined empirically, and is usually in the range of about 50 to about 500 hemagglutinin (HA) units/ml at final concentration in the tissue culture fluid. More preferably, viral concentration varies from 50–250 HA units/ml.

Interferon production is maximized by employing an Absorption/Dilution method in which the concentrated cell cultures are diluted. According to this method, the Sendai virus at a final concentration of about 375 HA units/ml is adsorbed to leukocytes at a cell density of $10^7$ cells/ml for approximately one hour at approximately 36° C. Preferably the culture is diluted about 2.5 fold thereafter with induction medium supplemented with agamma serum to a final cell density of 4×10 cells/ml and a Sendai virus concentration of about 150 HA units/ml. Under any conditions, induction using the Adsorption/Dilution method has been found to generate about 10% higher titer than those generated without the use of the Adsorption/Dilution method. The dilution medium may be either at room temperature or prewarmed to 36° C., and may or may not contain primers.

Inductions may optionally be performed without using the Adsorption/Dilution method. In those cases, the leukocytes at the indicated cell density (1–10×$10^6$ cells/mL) may be primed with crude interferon for about 3 hours followed by addition of Sendai virus at the indicated concentrations. The cultures are then incubated for 15–16 hours and interferons may be collected similarly.

Incubation temperatures of leukocyte cultures for interferon production according to this invention can range from about 35° C. to about 37° C. However, the optimal incubation temperature has been determined to be 36° C. The Cantell method recommends 37.5° C. as the optimal incubation temperature for interferon production [Mogensen et al., (1977); Cantell et al., Methods Enzymol., (1981); and Horowitz, (1986), all cited above]. However, the inventors found that a temperature lower than 37° C. produced more interferon. The results from inductions in triplicate 6-liter flasks at either 4 or 5×$10^6$ cells/ml, incubated at 35° C., 36° C. or 37° C. during entire induction process demonstrated that incubation at 36° C. produced 20% to 50% more interferon than that at 35° C. or 37° C.

The stirring speed of magnetic bar in the induction cultures is also important in order to maintain optimal aeration and mixing of components. At 72 rpm, about 17,000 IRMA U/ml of interferons are made in medium size flasks (500 ml) with 4×$10^6$ cells/ml. When stirring rates are increased to about 170 to 250 rpm, the amount of interferons produced significantly increased to about 30,000 IRMA U/ml. Therefore, a stirring rate of between 100 and 300 rpm, and preferably about 170 rpm, is necessary for maximum production of interferon during the induction steps.

Total incubation times after Sendai virus addition can range between 1 to 48 hours, and preferably between 15 to 22 hours. After the appropriate incubation time at 36° C., the suspension is centrifuged at about 2,500 rpm to remove cells and debris and a crude alpha interferon is collected.

Table 1 below summarizes the differences between the present method (A) for inducing alpha interferon and that previously reported [Cantell et al., (1981), cited above] (B).

Table 1

Induction Medium
A. Eagle's MEM supplemented with Earles's salts, L-glutamine, non-essential amino acids, 4.6 mg/ml Tricine, 24 µg/ml neomycin at pH 7.4

B. Eagle's MEM without phosphate and supplemented with 3 mg/ml Tricine, 24 μg/ml neomycin at pH 7.4

NaHCO$_3$, Hu Agamma Serum and Supplements

A. 0.1 to 2.5 mg/ml NaHCO$_3$, 0.1 to 1.5 mg/ml serum and Vitamin C, or Vitamin B$_3$ (Niacin)

B. 2.4 mg/ml serum only

Volume of Flask

A. 150-ml, 500-ml, 2-liter, 6 liter flasks. Volume of culture may vary from 5% to 100% of the flask capacity.

B. 2-liter or 6-liter flask. Volume of culture is less than 50% of the flask capacity.

Cell Density

A. $10^7$ cells/ml at priming and virus adsorption phase followed by dilution to about $4\times10^6$ cells/ml for 1 hour after virus addition. Or about $4\times10^6$ cells/ml at priming virus adsorption and during overnight incubation.

B. $10^7$ cells/ml

Primer and Priming Conditions

A. Crude alpha interferon supernatant or purified alpha interferon at 10–50 IU/ml; priming 3 hours at 36° C.

B. Crude alpha interferon supernatant at 100–200 IU/ml, priming 2 hours at 37.5° C.

Sendai Virus

A. 125–500 HA units/ml at the virus adsorption phase followed by dilution to 50–200 HA units/ml B. 100–150 HA units/ml Stirring Speed and Incubation Conditions A. 130–250 rpm; 15–20 hours at 36° C.

B. Unspecified; 17 hours at 37.5° C.

After induction, interferon titer is then assayed either by an immunoradiometricassay using IRMA kits [Celltech; Berkshire, UK], or in a cytopathic effect (CPE) assay using human epidermoid HEp-2 cells (ATCC CCL 23) and vesicular stomatitis virus (VSV, Indiana strain ATCC #VR-158) as a challenge virus according to the published method [Linette et al, *Cancer Therapy and Control*, 1:109–120 (1990)]. The titer determined by IRMA assay is given in IRMA U/ml or just U/ml and the titer obtained from CPE assay is presented as IU/ml (international units/ml) as compared with the National Institutes of Health leukocyte reference standard (G$_a$ 23-902-530). The IRMA assay employs a radiolabeled NK2 monoclonal antibody as the detecting antibody. Based on the species recognized by NK2, the IRMA titer will generally be lower than the CPE titer. It is generally observed that the IRMA titer of crude interferon from the induction is approximately half of the CPE titer.

b. Purification of Crude Interferon

The crude interferon is purified using the protocol described in detail in Example 2. Briefly, this process is as follows. First, the crude leukocyte cultures from the induction are either centrifuged at approximately 2,900×g for between about 15 to 20 minutes, or by filtration through suitable cartridge filter systems. The cartridge filter systems are comprised of, for example, pre-sterilized Polygard-CR high efficiency 0.1 μ pore size cartridge filters connected in series with 0.5 μ pore size Polysep-TP filters (Millipore Corporation, Bedford, Mass.).

The resulting crude alpha interferon supernatant is then concentrated between about 10 to 100 fold, generally by using a tangential flow filter system. A 50 fold concentration is preferred. The concentrated supernatent can then be centrifuged under conditions of about 9000×g for about 30 minutes. However, no additional centrifugation is required if filtration is used as the collection method.

The crude concentrated alpha interferon from this step is passed through a first column chromatography (an NK2 Antibody Affinity Column), from which alpha interferon is eluted at pH 2 after extensive washing. The antibody affinity chromatography, removes most of the human serum proteins and other impurities. Approximately 80–90% of interferon IRMA activity is recovered and interferon is purified 8,000 fold from this step. The purity of interferon at this stage is usually >90%.

The eluted alpha interferon is subjected to acid incubation for 5 days at 4° C., followed by neutralization, concentration, and gel filtration on a Column Chromatography (Superose 12 Column), resulting in the composition of the present invention. The gel filtration removes the high and lower molecular weight impurities, such as murine IgG leaked from NK2 column, human IgG, interferon oligomers, or degraded IFN.

Figure 3:
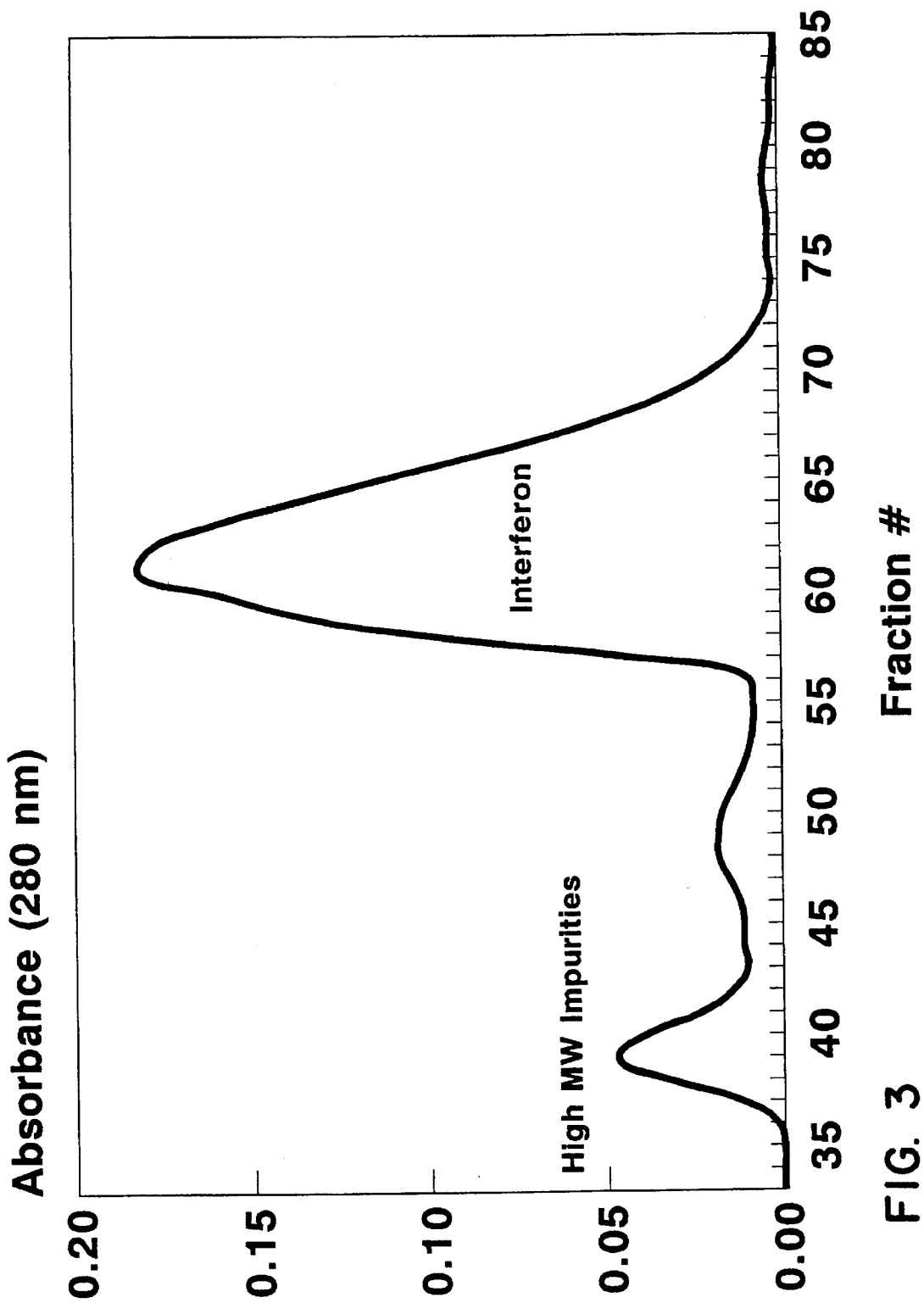
FIG. 3 depicts a typical elution profile of IFN-αn3a from Superose Column Chromatography.

A typical gel filtration chromatography elution profile is shown in FIG. 3 where interferons elute in the major absorbance peak. The total purification after both affinity and gel filtration chromatography steps results in a recovery of 60–70% of interferon IRMA activity and a total of about 12,000 fold purification. The final purified interferon is approximately 99% pure as determined by SDS-PAGE and Western Blot analysis, and has an antiviral specific activity of about $4\times10^8$ IU/mg (see Example 4A).

3. Pharmaceutical Compositions and Methods

The purified alpha interferon of this invention, IFN α-n3*a*, may be used to treat various diseases of the immune system, cancers and/or viral diseases. Treatment of conditions including, but not limited to, *Condyloma* acuminata, hepatitis B, hepatitis C, hairy cell leukemia, AIDS, Karposi's sarcoma, chronic fatigue syndrome, genital herpes, genital warts, cervical dysplasia, cervical carcinoma, and vaginal condyloma, using the alpha interferon of this invention is envisioned. The product may also be administered to treat other conditions susceptible to treatment with alpha interferon.

Pharmaceutical compositions of the invention, comprising an effective amount of the alpha interferon produced according to this invention in a pharmaceutically acceptable carrier, can be administered to a patient having a condition which is responsive to treatment with alpha interferon.

The therapeutic and pharmaceutical compositions of the present invention therefore comprise a therapeutically effective amount of IFN α-n3*a* in admixture with a pharmaceutically acceptable carrier. The pharmaceutical compositions having anti-viral, anti-cancer or immunomodulating activity may be utilized in conventional type formulations such as solutions, syrups, emulsions, injectables, tablets, capsules, topical formulations or suppositories.

Suitable carriers are well known to those of skill in the art of pharmaceutic science (see, e.g., Remington's Practice of Pharmacy). Exemplary carriers include sterile saline, and sugars such as xylitol, glycerol, lactose, and sucrose. Other carrier components include calcium phosphate, gelatin, dextrin, agar, cellulose, hydroxyethyl cellulose (for topical applications), petroleum jelly, polyethelyene glycol, pectin, peanut oil, olive oil, sesame oil, squalene and water.

Additionally, the carrier or diluent may include a time delay material, such as glyceryl monostearate or glyceryl distearate alone or with a wax. Optionally, suitable chemical stabilizers may be used to improve the stability of the pharmaceutical preparation. Suitable chemical stabilizers are well known to those of skill in the art and include, for example, citric acid and other agents to adjust pH, chelating or sequestering agents, and antioxidants.

The formulations of the pharmaceutical composition containing IFN α-n3*a* may conveniently be presented in a unit dosage form and may be prepared by any of the conventional methods. Alternatively, the composition may be in a form adapted for slow release in vivo, as is known in the art. All methods include the step of bringing into association the active ingredient with the carrier which may constitute one or more accessory ingredients.

The amount of the purified product which will be effective in the treatment of a particular disorder or condition will depend on the nature of the disorder or condition, and can be determined by standard clinical techniques. In one embodiment of this invention, it would be desirable to determine the cytotoxicity of a tumor type to be treated in vitro, and then in useful animal model systems prior to testing and use in humans.

Methods of introduction include, but are not limited to, intralesional, intradermal, intramuscular, intraperitoneal, intravenous, subcutaneous, topical, oral, and intranasal.

Further, it may be desirable to administer the pharmaceutical compositions of the invention locally to the area in need of treatment. This may be achieved by methods including, but not limited to, local infusion during surgery, by injection, by means of a catheter, or by means of an implant, said implant being of a porous, non-porous, or gelatinous material, including membranes, such as sialastic membranes, or fibers.

The invention also provides for pharmaceutical compositions comprising IFN α-n3a administered via liposomes, microparticles, or microcapsules. In various embodiments of the invention, it may be useful to use such compositions to achieve sustained release of the substances. In a specific embodiment, it may be desirable to utilize liposomes targeted via antibodies to specific identifiable tumor antigens (e.g., cell surface antigens selective for neuroblastoma or SCLC) [Leonetti et al, *Proc. Natl. Acad. Sci. USA*, 87:2448–2451 (1990); Renneisen et al, *J. Biol. Chem.*, 265:16337–16342 (1990)].

The alpha interferon of the present invention may also be employed in accordance with the methods and compositions of this invention, alone or in combination with other therapeutic or diagnostic agents useful in the direct or adjunctive treatment of certain cancers, immune disorders or viral diseases. It is contemplated that IFN α-n3a may be used in combination with other agents, e.g., antimetabolites, alkylating agents, vinca alkaloids, antineoplastic antibiotics, platinum derivatives, substituted ureas, adrenocortico steroids, cytokines, interleukins, AZT, ddI, ddC, other interferons, other anti-viral or anti-tumor agents or antibodies.

The dosage regimen involved in administering an effective amount of IFN α-n3a in a method for treating the above-described conditions will be determined by the attending physician considering various factors which modify the action of drugs, e.g. the condition, body weight, sex and diet of the patient, the severity of the tumor, time of administration and other clinical factors. The dosage of the compositions of the invention used to treat the specific disease conditions described herein may be varied depending on the particular disease and the stage of the disease. For example, for warts the composition is expected to be used at a dosage of equal to, or less than, the IFN alfa-n3 dosage of 0.25 million units (MU)/wart. For treatment of AIDS or other diseases requiring more aggressive treatment, an appropriate dose may be considerably less than the 30–36 MU indicated for presently approved recombinant alpha interferons. More specifically, it is anticipated that the dosage for such conditions would range between about 1 million units to 15 million units.

Dosages may generally be administered three times a week. Other dosages and regimens may be determined by one of skill in the art with the application of routine skill.

In addition to treating the mammalian disorders described hereinabove, the methods and compositions of this invention may be utilized for veterinary purposes in the treatment of cancers, immune disorders or viral diseases that afflict horses, swine, cattle, canines, felines and fowl, for example. These disorders may be treated using quantities of the compound that may be used in treating the mammalian disorders described hereinabove.

The following examples are for illustrative purposes only, and should not be construed as limiting this invention in any way.

EXAMPLE 1 - METHOD OF PRODUCING IFN α-n3a - INDUCTION

For the preparation of bully coats, 500 units of human PBLs are obtained from FDA-approved blood centers. Red blood cells are then lysed using an ammonium chloride treatment (0.83%) according to Cantell et al., (1981), cited above.

Ammonium chloride-treated buffy coats are resuspended in 1x Eagle's MEM containing Earle's salts (Gibco 410-1500), L-glutamine, non-essential amino acids, 4.46 mg/ml Tricine (Aldrich), pH 7.4, 2.2 mg/ml sodium bicarbonate (Fisher), 24 µg/ml of Neomycin Sulfate, and 0.4 mg/ml of human agamma serum (NABI).

Leukocytes ($10^7$ cells/ml) are suspended in ix MEM and 20 units/ml of crude alpha interferon are added as a primer. The crude alpha interferon is the product resulting from the induction steps described herein, without purification, adjusted with HCl to pH2 for five days to inactivate any adventitious agents or potential viral contaiminants.

This suspension is incubated in 6 liter sterile glass flasks. Leukocytes are primed for 3 hours at 36° C. followed by addition of the Sendai virus (Cantell strain from SPAFAS; Storr, Conn.) at a final concentration of 150 HA units/ml.

After 1 hour incubation to allow virus attachment, leukocytes are diluted to $4\times10^6$ cells/ml (2.5 fold) with the same medium containing agamma serum, sodium bicarbonate and no primer. This is followed by an additional 15 hours incubation at 36° C. Cells and debris are then removed by centrifugation at 2,500 rpm (Beckman model J6-B) and crude interferon titers are then assayed by IRMA or CPE assays as previously described above.

EXAMPLE 2 - METHOD OF PRODUCING IFN α-n3a-PURIFICATION

All purification steps are performed at 2°–8° C. unless otherwise indicated.

A. Collection/Concentration of Crude Interferon

After incubation for 15–20 hours, the leukocytes are removed from the induction cultures of Example 1 by centrifugation at approximately 2,900×g for 15–20 minutes. The supernatant (crude interferon solution) is reserved and the leukocytes discarded. If not to be processed immediately, the supernatant is stored in sterilized containers at 4° C.

The crude interferon solution is concentrated at 50 fold, using a tangential flow filter system with a nominal molecular weight cut off of 10,000. The concentrated interferon is centrifuged at approximately 9,000×g for about 30 minutes. The concentrated interferon can be stored at −70° C.

B. Affinity Purification

1. Preparation of Chromatography Columns

This purification method uses monoclonal antibody specific to human alpha interferons, e.g. NK2 produced by Celltech Limited (Slough, England). The monoclonal antibody is coupled to CNBr activated Sepharose-4B (e.g., Reselute NK2) and stored at 4° C. The size of the affinity column is dependent on the binding capacity of the affinity gel for interferon, which is determined on each preparation.

Columns are prepared by pouring an appropriate amount of Sepharose-antibody gel into a suitable glass column. The monoclonal antibody column is washed with approximately 5 column volumes of phosphate buffered saline followed by washing with 3 column volumes of a solution containing 0.1M citric acid and 0.3M sodium chloride at pH 2. The pH of the column is then neutralized to 7.4 by washing with 3 column volumes of phosphate buffered saline (PBS). This pre-wash cycle may be repeated for a couple more times.

2. Preparation of Concentrated Crude IFN

The concentrated crude interferon is clarified by centrifugation at approximately 17,700×g for 60 minutes and is filtered utilizing appropriate cartridge 0.22 or 0.45 micron filters prior to loading onto monoclonal antibody column.

3. Affinity Purification

Approximately 150 million units of crude filtered interferon is loaded per ml of affinity gel. Interferon units are determined by IRMA (Celltech Ltd.). The column is washed with approximately 1.5 column volumes of phosphate buffered saline followed by 10 column volumes of a 20 mM phosphate buffer (pH 7.4) containing 50% (v/v) ethylene glycol and 1.5M sodium chloride. The washes are completed with a final 10–30 column volumes of phosphate buffered saline. The interferon is eluted from the affinity column with a solution containing 0.1M citric acid and 0.3M sodium chloride (pH 2).

4. Regeneration of Affinity Column

The monoclonal antibody column is washed with 3–5 column volumes of phosphate buffered saline until the pH of the eluate is neutral. For storage of column, the column is washed with 3–5 column volumes of phosphate buffered saline containing 0.1% sodium azide.

C. Acid Incubation and Neutralization

The eluted interferon solution (about pH 2) from the monoclonal affinity column is incubated at 4° C. for a minimum of 5 days. This acid incubation step is necessary to inactivate any potential adventitious agents, such as HIV-1. After 5 days storage period the pH of the solution is adjusted to 7.4 with 1.0M Tris.HCl (hydroxymethylaminomethane). The interferon protein in the solution is concentrated to approximately 1–3 mg/ml.

D. Gel Filtration

The preparative grade Superose 12 beads (Pharmacia, Piscataway, N.J.) are used for the gel filtration chromatography. Concentrated interferon in 5% of the column volume is loaded and eluted with phosphate buffered saline. All fractions constituting the main peak containing interferon are aseptically pooled. The purified interferon is filtered using a 0.2 micrometer or smaller low binding filter and stored at −70° C.

E. Results

Results from a typical purification procedure are shown in Table 2 indicating purification step (Purifn Step), total volume and mass of proteins, total activity, which is indicated as the number in the column multiplied by $10^9$ Units, percentage yield as determined by the total IRMA units recovered at each step, specific activity (Spec. Actvy) measured in million units (MU)/mg, and fold purification (Purifn. Fold). Interferon activity is determined by immunoradiometric assay [Celltech, Ltd.] which uses radiolabeled NK2 as the detecting antibody.

TABLE 2

Interferon Purification Yield from a Typical Experiment

| Purifn Step | Protein Total Vol (L) | Mass (mg) | Interferon Activity Total Act'y[1] | % Yield | Spec. Actvy (MU/mg) | Purifn Fold |
|---|---|---|---|---|---|---|
| Crude IFN | 212.4 | $8.5 \times 10^4$ | 4.6 | 100 | 0.054 | 1 |
| Concentration | 5.15 | $7.1 \times 10^4$ | 4.5 | 99 | 0.064 | 1 |
| NK2 Affin'y Chromatog'y | 0.073 | 9.4 | 4.0 | 87 | 430 | 7,990 |
| Neutraliz'n Concentra'n | 0.0073 | 7.3 | 3.4 | 74 | 470 | 8,740 |
| Superose Chromatog'y | 0.045 | 4.8 | 3.2 | 70 | 660 | 12,200 |

EXAMPLE 3 - RP-HPLC ASSAY

In this example alpha interferon species in the composition are separated according to their relative hydrophobicity using RP-HPLC [Janssen et al., *J. Chromatographic. Sci.*, 22:234 (1984); Stone et al., *J. Chrom.* 359:203 (1986)]. The separation was achieved by increasing acetonitrile concentration. The least hydrophobic interferon species eluted as early peaks and the most hydrophobic interferon species eluted later.

Figure 4A:
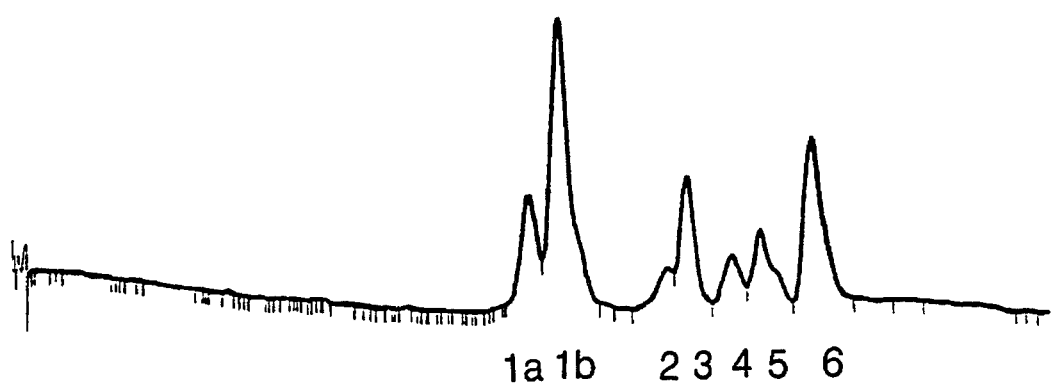
FIG. 4A depicts a typical RP-HPLC profile of IFN α-n3a from a semi-preparative $C_4$ column (10×250 mm), illustrating peaks 1a, 1b, and 2 through 6.
Figure 4B:
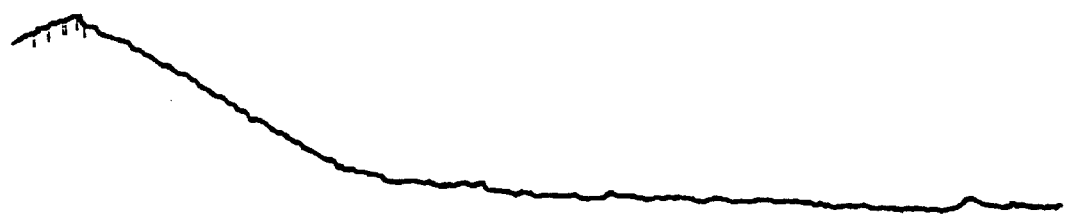
FIG. 4B depicts a comparative blank gradient RP-HPLC profile.

The typical RP-HPLC profile has been obtained from the semi-preparative column runs, as shown in FIG. 4, as follows. Approximately 1–2 mg of purified interferon IFN α-n3a was fractionated on a semi-preparative VYDAC® C4 hydrocarbon reverse phase high pressure liquid chromatography (HPLC) column (5 µ/300 Å, 10×250 mm). The elution gradient used for the semi-preparative $C_4$ RP-HPLC is shown below in Table 3. The gradient was linear, with the buffers as follows: A:90% $H_2O$/10% ACN/0.1% TFA v/v/w; and B:90% ACN/10% $H_2O$/0.1 TFA v/v/w.

TABLE 3

| TIME | FLOW RATE | % A | % B |
|---|---|---|---|
| initial | 5.0 ml/min | 95 | 5 |
| 15 min | 5.0 ml/min | 60 | 40 |
| 59 min | 5.0 ml/min | 50 | 50 |
| 60 min | 5.0 ml/min | 10 | 90 |
| 65 min | 5.0 ml/min | 10 | 90 |
| 66 min | 5.0 ml/min | 95 | 5 |
| 76 min | 5.0 ml/min | 95 | 5 |

TABLE 3-continued

| TIME | FLOW RATE | % A | % B |
|---|---|---|---|
| 79 min | 0.04 ml/min | 95 | 5 |

The purified interferon was fractionated into 7 peaks, i.e. Peaks 1a, 1b, 2, 3, 4, 5 and 6. The first peak resolved into two partially overlapping peaks, i.e. 1a and 1b. These two peaks were characterized separately in all analyses. The proteins in each peak were collected individually.

Table 4 presents the relative proportion of each peak from a typical RP-HPLC profile.

TABLE 4

Area Percentages of RP-HPLC peaks of IFN α-n3a

| Peak # | % of Total |
|---|---|
| 1a | 13 |
| 1b | 36 |
| 2 | 4 |
| 3 | 15 |
| 4 | 5 |
| 5 | 10 |
| 6 | 17 |

As indicated above, peaks 2 and 4 contain small quantities of material. Peak 2 was not further characterized for amino acid composition and carbohydrate content. Peak 4 was not further characterized for aminosugar content following HCl hydrolysis.

After lyophilization, the interferon in each peak was reconstituted in 25 mM Tris-HCl buffer at pH 7.0. The reconstituted material was then pooled accordingly from all column runs for subsequent analyses.

EXAMPLE 4 - BIOLOGICAL ASSAYS

A. Antiviral Assay:

An antiviral assay was performed using three different cell lines: 1) human HEp-2 [ATCC CCL 23], 2) bovine MDBK [ATCC CRL 6071], and 3) rabbit RK-13 [ATCC CCL 37] cells. The interferon was serially two-fold diluted in 96-well plates, followed by addition of 30,000 cells/well. After an overnight incubation, cells were infected with VSV (Indiana strain ATCC #VR-158), followed by an additional overnight incubation. Cytopathic effect (CPE) is checked microscopically on virus control, cell control and cells which received standard interferon. Cells were stained with crystal violet when the wells containing standard interferon showed proper CPE. For all samples, 50% cytopathic effect is measured visually, and interferon titer is calculated by comparison to the laboratory standards which had been previously standardized against the NIH interferon reference standard (Ga 23-902-530). The results are reported in Table 5 below.

B. Antiproliferative Assay

Antiproliferative assay is measured in human lymphoblastoid Daudi cells. Interferons are serially 5 fold diluted in 96-well plates (100 μl/well) followed by addition of $10^4$ Daudi cells/well (in 100 μl). After 40 hours incubation, cells are treated with 1.5 μCi/well (in 25 μl) of $^3$H-thymidine for 7 hrs. Thymidine uptake is measured by harvesting and washing cells with water on glass fiber filters followed by measurement of incorporated radioactivity using a scintillation counter. Again, titers are calculated and corrected against laboratory standards.

C. Assay Results

The antiviral and anti-proliferative characteristics of unfractionated IFN α-n3a and the RP-HPLC peaks are presented below in Table 5.

TABLE 5

Specific Activities of IFN α-n3a RP-HPLC Peaks

| Peak # | MU/mg IFN CPE | | | AP |
|---|---|---|---|---|
| | HEp-2 | MDBK | RK-13 | Daudi |
| 1a | 252.0 | 262.9 | 0.08 | 86.9 |
| 1b | 195.6 | 265.0 | 0.17 | 109.4 |
| 2 | 269.8 | 278.1 | 0.77 | 127.5 |
| 3 | 377.3 | 316.8 | 7.09 | 175.7 |
| 4 | 589.9 | 345.1 | 2.63 | 216.4 |
| 5 | 298.6 | 362.7 | 1.56 | 205.5 |
| 6 | 884.1 | 447.7 | 0.59 | 237.9 |
| Unfractionated IFN α-n3a | 502.0 | 426.7 | 1.94 | 149.2 |

The specific biological activity is presented as the number of biological units per mg of the total protein present. The data in Table 5 show that the specific CPE activities on human HEp-2 and bovine MDBK cells are similar in each peak. The specific antiproliferative activity on Daudi cells is approximately 2 fold less than the antiviral activities in each peak. When the interferon was assayed on rabbit kidney cells (RK-13), some CPE activity was detected. The specific activity is at least 100 to 1000 fold lower than that on human or bovine cells. Interestingly, the interferon in peak 3 has the highest specific activity on RK-13 cells.

Figure 5:
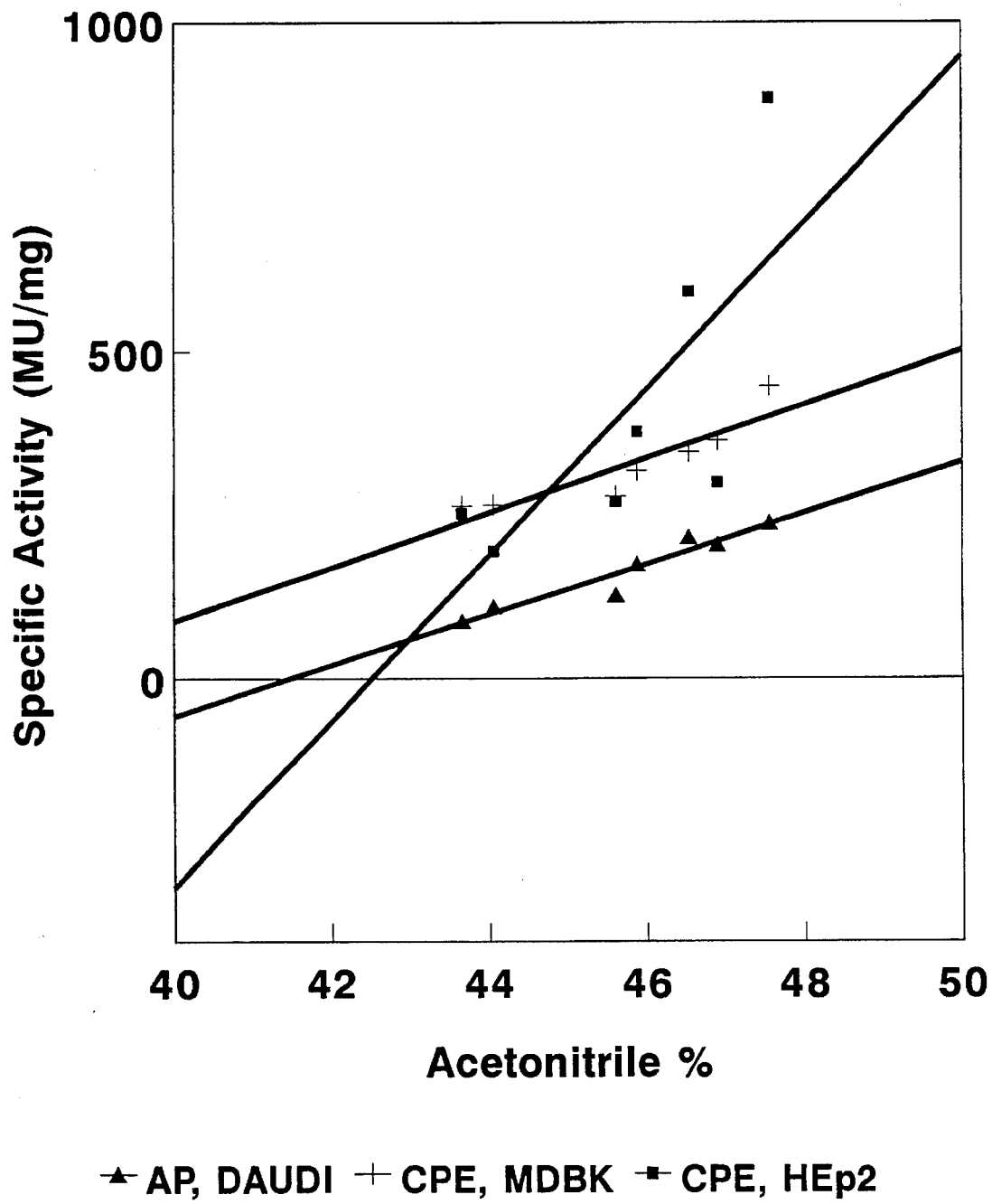
FIG. 5 depicts the correlation between the biological activity and hydrophobicity of proteins in RP-HPLC peaks.

The data presented in Table 5 also demonstrate that the earlier eluting peaks, such as peaks 1a and 1b, contained lower specific activities on HEp-2, MDBK and Daudi cells. When peak 1(a and b) was tested in this assay, it constituted only about 25% of the total antiviral activity of the IFN α-n3a composition. The later eluting peak 6 contains the highest specific activities. In fact, when the specific activity is plotted against the percent of acetonitrile in the elution gradient (see FIG. 5), a direct correlation is seen between the increase in specific activity and the relative increase in hydrophobicity of the alpha interferon protein. The more hydrophobic the interferon is, the higher specific activity it has. One can speculate that the more hydrophobic interferon subspecies may bind to the interferon receptor(s) with a higher affinity or initiate cellular events more efficiently and therefor show a higher specific activity.

EXAMPLE 5 - PHYSICAL PROPERTIES OF IFN α-n3a

The interferon proteins in the seven peaks fractionated on reverse phase HPLC were characterized by SDS-PAGE.

A. One dimensional SDS-PAGE

1. Methods

One dimensional SDS polyacrylamide gel electrophoresis (SDS-PAGE) analyses were performed using procedures similar to those described by Laemmli, Nature, 277:680 (1970). The IFN α-n3a was analyzed in 14.5% SDS-PAGE under both reducing and non-reducing conditions. The protein bands are visualized by Coomassie blue staining. A Western blot of duplicated SDS gel was immunostained with LIT-1 murine monoclonal antibody specific to human IFN alpha and developed as described [Towbin et al. Proc. Natl. Acad Sci. (USA)

76:4350 (1979); and Haid et al., *Meth. Enzymol.*, 96:192 (1983)].

2. Results

Figure 6:
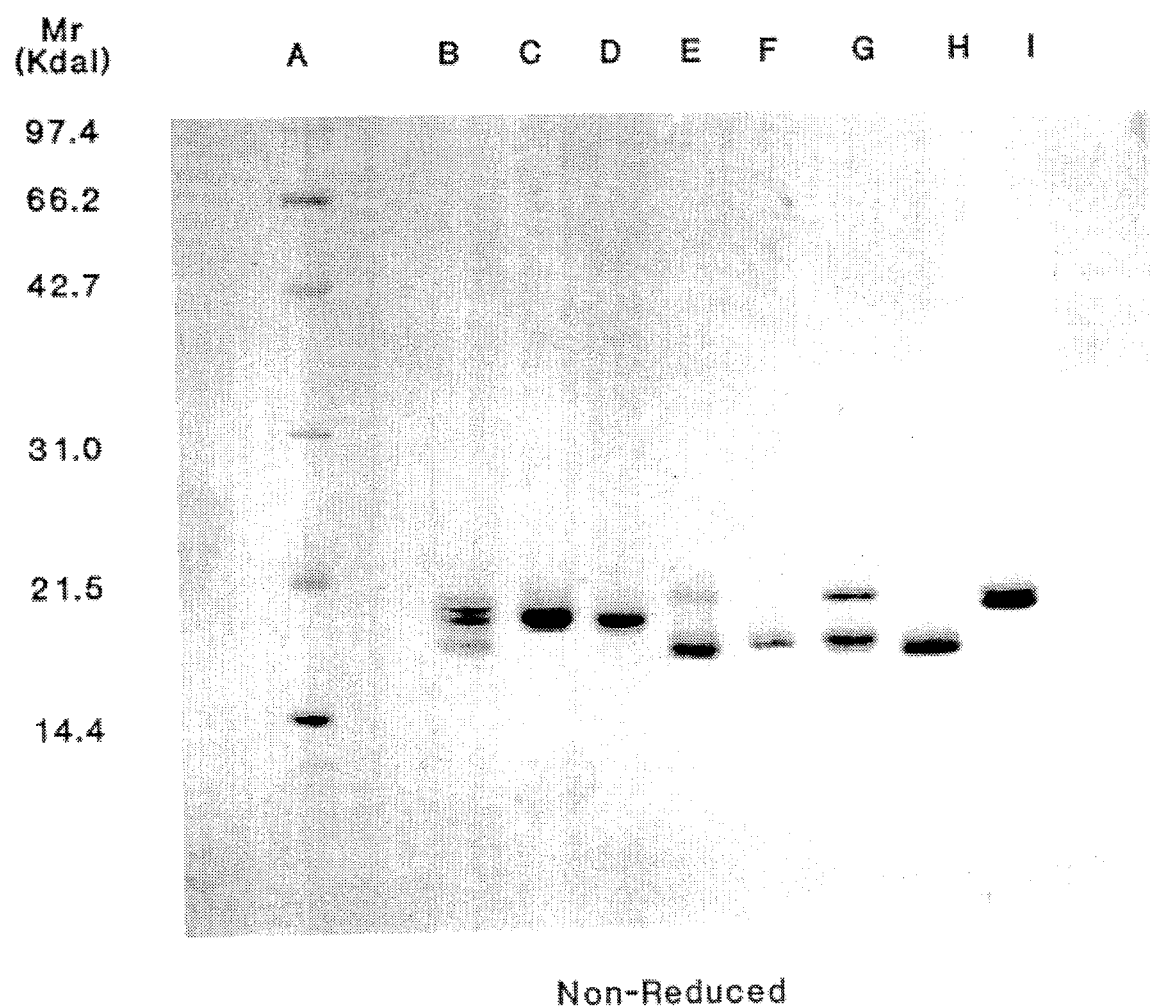
FIG. 6 illustrates the Coomassie blue stained SDS-PAGE of IFN α-n3a under non-reducing conditions. Column A illustrates prestained low molecular weight markers (Biorad). Column B is IFN α-n3a (unfractionated). Column C is RP-HPLC Peak 1a. Column D is RP-HPLC Peak 1b. Column E is RP-HPLC Peak 2. Column F is RP-HPLC Peak 3. Column G is RP-HPLC Peak 4. Column H is RP-HPLC Peak 5. Column I is RP-HPLC Peak 6.
Figure 7:
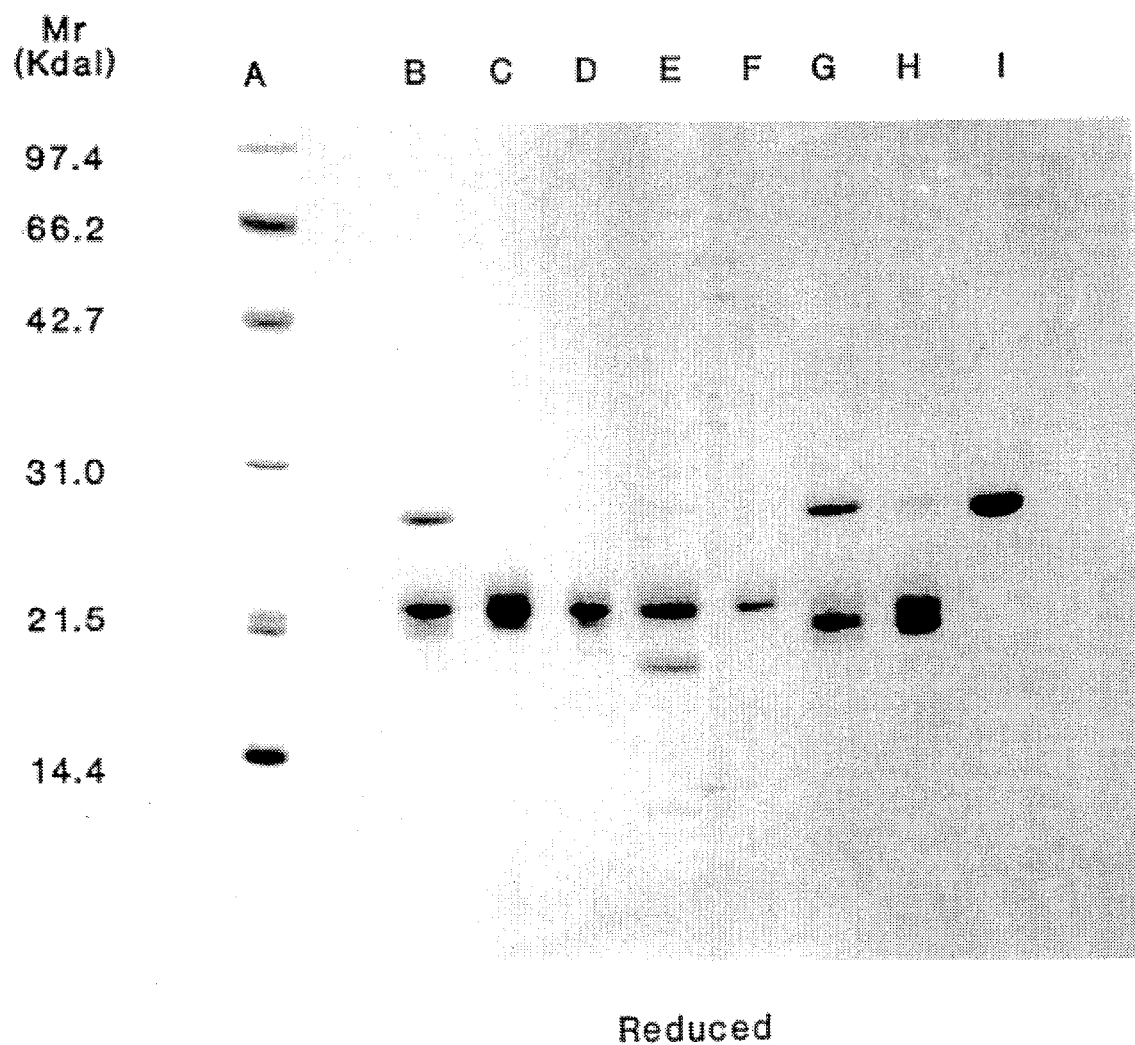
FIG. 7 illustrates the Coomassie blue stained SDS-PAGE of IFN α-n3a under reducing conditions. The columns are as defined above in FIG. 6.

The data for non-reducing and reducing SDS-PAGE profiles are summarized below, in Tables 6 and 7, respectively. In addition, FIGS. 6 and 7 show the Coomassie blue stained SDS-PAGE profiles under non-reducing and reducing conditions, respectively.

TABLE 6

SDS-PAGE (Non-reduced)
Relative Molecular Weights and Area Percentages

| Molecular Weight (KD) | Relative Area Percent (%) | | | | | | | |
|---|---|---|---|---|---|---|---|---|
| | Unfract'd IFN | RP-HPLC peaks of Interferon | | | | | | |
| | | 1a | 1b | 2 | 3 | 4 | 5 | 6 |
| 19.3 | 17.1 | — | — | 17.8 | — | 36.5 | 1.6 | 29.8 |
| 19.0 | 27.4 | — | — | — | — | — | 1.2 | 70.2 |
| 18.5 | 26.3 | 93.8 | 93.1 | — | — | — | — | — |
| 18.0 | 6.5 | 6.2 | 4.8 | — | — | — | — | — |
| 17.8 | — | — | 2.1 | 18.3 | 17.1 | 52.0 | 21.0 | — |
| 17.7 | 19.2 | — | — | — | 82.9 | — | — | — |
| 17.5 | 3.4 | — | — | 57.2 | — | 11.6 | 76.2 | — |
| 17.2 | — | — | — | 6.8 | — | — | — | — |

TABLE 7

SDS-PAGE (Reduced)
Relative Molecular Weights and Area Percentages

| Molecular Weight (KD) | Relative Area Percent (%) | | | | | | | |
|---|---|---|---|---|---|---|---|---|
| | Unfract'd IFN | RP-HPLC peaks of Interferon | | | | | | |
| | | 1a | 1b | 2 | 3 | 4 | 5 | 6 |
| 27.7 | — | — | — | — | — | — | 2.3 | — |
| 27.5 | — | — | — | 0.9 | — | — | — | — |
| 27.0 | 23.8 | — | — | — | — | 34.3 | — | 100.0 |
| 22.3 | — | — | — | — | 16.8 | — | — | — |
| 21.7 | 58.1 | — | — | — | 83.2 | 17.6 | — | — |
| 21.5 | — | 92.4 | 80.8 | 73.4 | — | — | 40.8 | — |
| 20.8 | 9.4 | 7.6 | 13.2 | — | — | 41.7 | — | — |
| 20.0 | 4.1 | — | 2.8 | — | — | 6.4 | 56.9 | — |
| 19.4 | 1.3 | — | 3.2 | — | — | — | — | — |
| 19.0 | 1.5 | — | — | — | — | — | — | — |
| 18.6 | 1.7 | — | — | 22.4 | — | — | — | — |
| 13.0 | — | — | — | 3.3 | — | — | — | — |

The data in Tables 6 and 7 demonstrate heterogeneity (i.e. there is more than one protein band) in most of the peaks. Under reducing conditions only, peak 6 appears to contain a single protein band by this method. Peaks 1a and 1b contain proteins with similar molecular weights under both reducing and non-reducing conditions. These two peaks, 1a and 1b, also contain the same major interferon species, i.e. IFN-α2b, as demonstrated by partial amino acid sequencing.

The relative number of interferon protein bands in each peak was determined by laser densitometry. The relative molecular weights were calculated by comparing with the molecular weight markers.

Figure 8:
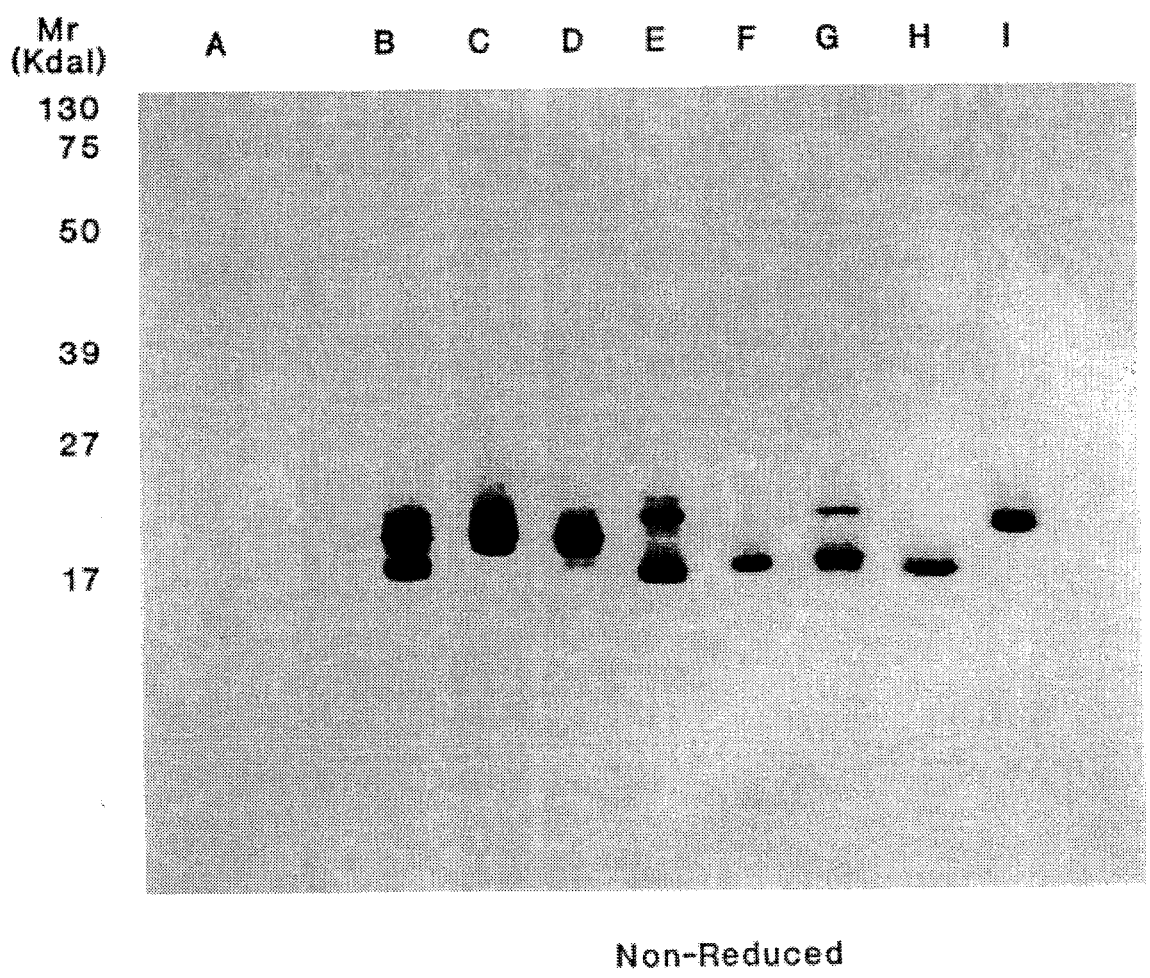
FIG. 8 illustrates the immunostained Western Blot of IFN α-n3a under non-reducing conditions. The columns are as defined above in FIG. 6.
Figure 9:
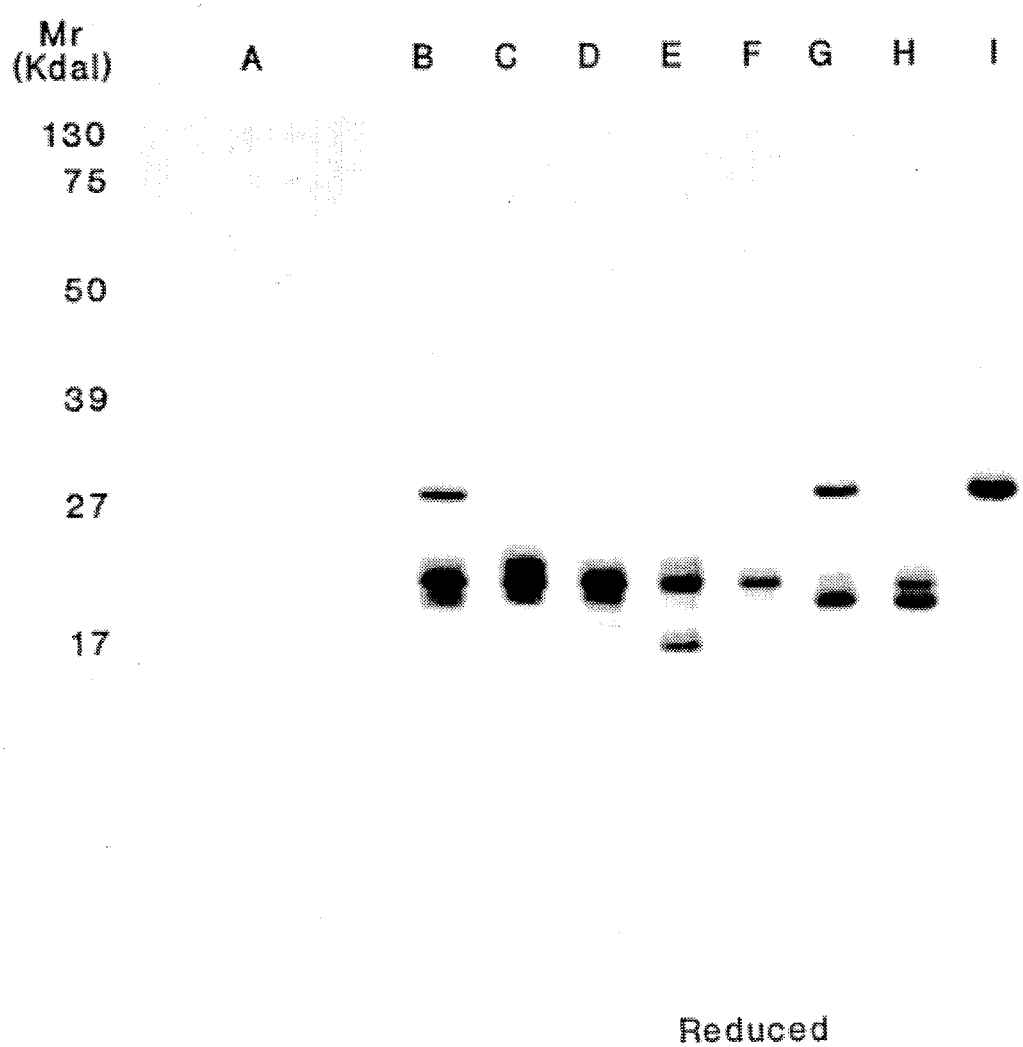
FIG. 9 illustrates the immunostained Western blot of IFN α-n3a under reducing conditions. The columns are as defined above in FIG. 6.

The results from Western blot analyses are presented in FIGS. 8 and 9 for the non-reducing and reducing conditions, respectively. The data show that every protein band detectable by Coomassie blue staining was recognized by the LIT-1 monoclonal antibody. This demonstrates that all protein bands in each peak are identified as human alpha interferons. The impurity level in unfractionated interferon is approximately 1%. After fractionation on RP-HPLC, this low level of impurity was not detectable in any of the peaks.

Characterization continued with two-dimensional gel analysis.

B. Two-Dimensional SDS-PAGE

1. Methods

Two dimensional gel electrophoresis includes the isoelectric focusing in the first dimension and SDS-PAGE in the second dimension. For the first dimensional analysis, 5–10 µg of interferon from each RP-HPLC peak was loaded onto an acrylamide/urea gel casted in a glass tube (2×180 mm). The tube gel is run at constant voltage of 400 volts for 16 hours followed by 800 volts for 1 hour. The ampholines (Millipore) with a pH range between 3 and 10 are used for isoelectric focusing analysis. The tubular gel was then extruded from the glass tube, equilibrated in SDS sample buffer and layered on a 15% SDS-polyacrylamide slab gel for the second dimensional analysis. The SDS-PAGE is run in a Tris/glycine buffer at pH 8.3 at constant current of 35 mA. The proteins in the 2-D gels were visualized by silver staining. Interferon protein was identified by immunostaining with LIT-1 monoclonal antibody.

2. Results

The results of the two-dimensional gel analyses for unfractionated IFN α-n3a as well as the protein in each RP-HPLC peak show that there are multiple spots detected for all samples. The unfractionated IFN α-n3a has approximately 30 spots by 2-D gel analysis. All spots are recognized by LIT-1 monoclonal antibody, indicating that they are indeed interferon proteins. The number of spots and molecular weights for proteins in each of the peaks are summarized in Table 8 below. The isoelectric points for all interferon proteins in IFN α-n3a are within the pI range of 5.0 to 7.5.

TABLE 8

Analysis of 2-D Gel Profiles

| Peak # | Number of Spots* | Molecular Weight (Kdal) |
|---|---|---|
| IFN** | 30–35 | 17.7–27.8 |
| 1a | 8–10 | 20.6–22.8 |
| 1b | 8–11 | 18.9–22.8 |
| 2 | 3–4 | 22.8 |
| 3 | 4–5 | 21.9–22.8 |
| 4 | 6–9 | 21.9–27.8 |
| 5 | 5–7 | 21.9–22.8 |
| 6 | 1 (smear) | 27.8 |

*Stained with Silver Stain and Immunostain
**Unfractionated

The 2-D gel profiles for peaks 1a and 1b appear to be very similar. There is little difference in molecular size and charge. They may elute separately on RP-HPLC due to some non-charge related modifications of the proteins. The 2-D gels for the rest of peaks are quite different from each other. The profile for each peak has its own characteristics. The multiple spots present in each peak indicate the heterogeneous population of proteins. This heterogeneity may be due to differences in translation and/or post-translational modifications of the proteins.

EXAMPLE 6 - BIOCHEMICAL PROPERTIES OF IFN α-n3a

A. Amino Acid Composition

Interferon protein was hydrolyzed in 6N HCl at 104° C. for 24 hours in a Pico-Tag heating block. The hydrolysates were dried under vacuum and derivatized with 10% phenylisothiocyanate (PITC) in a solution of 70% ethanol, 10% water and 10% triethylamine. The resulting phenylthiocyanate (PTC) amino acids were separated by Pico-Tag C18 HPLC column. Elution of the PTC-amino acids was carried out with a 0–60% linear gradient of acetonitrile in water containing 140 mM sodium acetate (pH 6.4) and 0.05% triethylamine. The absorbance of PTC amino acids was measured at 269 nm. Absorbance data from each analysis were digitally acquired and stored in a microcomputer. The amino acid residues, cySteine and tryptophane, do not get modified by PITC in this reaction and hence do not give a signal. The data were then analyzed for amino acid identification and quantitation using the Water's Expert software package.

The results from the amino acid composition analyses for alpha interferon and individual RP-HPLC peaks are presented in Table 9. Table 9 shows that in general the amino acid compositions of individual peaks are similar to that of unfractionated interferon and to those species recognized by NK-α2 monoclonal antibody. When the composition of each peak is compared with the theoretical composition of specific subspecies identified by N-terminal sequencing there is agreement within ±1 residue. These data strongly support the identity of the major subspecies determined by N-terminal sequencing.

TABLE 9

Amino Acid Composition of IFN α-n3a and RP-HPLC Peaks

| | Amino Acid | Alpha Interferon Subspecies | | | | | | | | | | | | | | | | | |
| --- | --- | --- | --- | --- | --- | --- | --- | --- | --- | --- | --- | --- | --- | --- | --- | --- | --- | --- | --- |
| | | IFN α2 | | | IFN α8 | | | IFN α10 | | IFN α4 | | IFN α17 | | | | IFN α7 | | | IFN α16 | IFN α21 | |
| Col. # | Residues | 2a | 2b | 2c | 8a | 8b | 8c | 10a | 10b | 4a | 4b | 17a | 17b | 17c | 17d | 7a | 7b | 7c | α16 | 21a | 21b |
| 1 | Asx | 12 | 12 | 12 | 16 | 15 | 16 | 14 | 14 | 13 | 13 | 14 | 14 | 14 | 14 | 12 | 12 | 12 | 14 | 13 | 13 |
| 2 | Glx | 26 | 26 | 26 | 28 | 28 | 27 | 29 | 29 | 29 | 28 | 29 | 29 | 29 | 29 | 29 | 30 | 29 | 26 | 29 | 29 |
| 3 | Ser | 14 | 14 | 14 | 15 | 16 | 15 | 14 | 13 | 14 | 14 | 14 | 14 | 14 | 13 | 13 | 13 | 13 | 13 | 14 | 14 |
| 4 | Gly | 5 | 5 | 5 | 2 | 2 | 2 | 5 | 5 | 5 | 5 | 5 | 5 | 5 | 5 | 4 | 3 | 4 | 4 | 5 | 5 |
| 5 | His | 3 | 3 | 2 | 3 | 3 | 3 | 3 | 3 | 5 | 5 | 2 | 3 | 3 | 3 | 4 | 4 | 4 | 4 | 3 | 3 |
| 6 | Arg | 9 | 10 | 11 | 10 | 10 | 9 | 13 | 13 | 11 | 11 | 10 | 10 | 11 | 11 | 12 | 13 | 12 | 15 | 10 | 10 |
| 7 | Thr | 11 | 11 | 11 | 6 | 6 | 6 | 7 | 8 | 8 | 9 | 9 | 9 | 9 | 9 | 8 | 8 | 9 | 8 | 8 | 8 |
| 8 | Ala | 8 | 8 | 8 | 9 | 9 | 9 | 9 | 9 | 10 | 9 | 9 | 9 | 9 | 9 | 9 | 9 | 9 | 8 | 9 | 9 |
| 9 | Pro | 5 | 5 | 5 | 4 | 4 | 4 | 5 | 5 | 4 | 4 | 6 | 5 | 5 | 6 | 5 | 5 | 5 | 4 | 5 | 5 |
| 10 | Tyr | 5 | 5 | 5 | 5 | 5 | 5 | 4 | 4 | 4 | 4 | 4 | 4 | 4 | 4 | 4 | 4 | 4 | 5 | 3 | 3 |
| 11 | Val | 7 | 7 | 7 | 7 | 7 | 7 | 7 | 7 | 7 | 8 | 6 | 6 | 6 | 6 | 7 | 7 | 7 | 9 | 8 | 8 |
| 12 | Met | 5 | 5 | 5 | 4 | 5 | 5 | 4 | 4 | 4 | 4 | 5 | 5 | 5 | 5 | 5 | 5 | 4 | 6 | 5 | 4 |
| 13 | Cys | 4 | 4 | 4 | 4 | 4 | 4 | 4 | 4 | 4 | 4 | 4 | 4 | 4 | 4 | 4 | 4 | 4 | 4 | 4 | 4 |
| 14 | Ile | 8 | 8 | 8 | 10 | 10 | 10 | 10 | 11 | 8 | 8 | 9 | 9 | 8 | 8 | 8 | 8 | 8 | 6 | 9 | 9 |
| 15 | Leu | 21 | 21 | 21 | 22 | 22 | 21 | 20 | 19 | 20 | 20 | 21 | 21 | 21 | 21 | 19 | 19 | 19 | 20 | 18 | 19 |
| 16 | Phe | 10 | 10 | 10 | 10 | 10 | 10 | 9 | 9 | 10 | 10 | 9 | 9 | 9 | 9 | 12 | 12 | 12 | 9 | 11 | 11 |
| 17 | Lys | 11 | 10 | 10 | 10 | 10 | 8 | 7 | 7 | 8 | 8 | 8 | 8 | 8 | 8 | 9 | 8 | 9 | 8 | 10 | 10 |
| 18 | Trp | 2 | 2 | 2 | 1 | 1 | 1 | 2 | 2 | 2 | 2 | 2 | 2 | 2 | 2 | 2 | 2 | 2 | 3 | 2 | 2 |

| Col. # | Unfrac. IFN α-n3a | RP-HPLC Peaks | | | | | | |
| --- | --- | --- | --- | --- | --- | --- | --- | --- |
| | | 1a | 1b | 2 | 3 | 4 | 5 | 6 |
| 1 | 12 | 11.6 | 10.3 | NA | 13.4 | 13.7 | 7.7 | 14.8 |
| 2 | 25.2 | 23.5 | 22.1 | NA | 27.8 | 23.9 | 24.2 | 27.8 |
| 3 | 14.1 | 14.7 | 14.7 | NA | 13.0 | 14.6 | 15.4 | 14.2 |
| 4 | 4.7 | 5.5 | 5.7 | NA | 5.3 | 4.2 | ND | 2.5 |
| 5 | 2.8 | 3.1 | 2.6 | NA | 2.7 | 2.8 | 3.0 | 3.0 |
| 6 | 10.4 | 10.4 | 10.6 | NA | 11.9 | 11.0 | 11.3 | 10.2 |
| 7 | 8.9 | 10.7 | 10.7 | NA | 6.3 | 6.8 | 8.9 | 5.6 |
| 8 | 9.3 | 8.8 | 8.7 | NA | 8.7 | 8.5 | 9.7 | 9.0 |
| 9 | 9.1 | 4.9 | 6.0 | NA | 8.3 | ND | 4.5 | 5.0 |
| 10 | 4.4 | 5.0 | 5.8 | NA | 4.0 | 4.0 | 5.1 | 5.4 |
| 11 | 6.0 | 6.1 | 6.2 | NA | 5.4 | 5.4 | 5.5 | 5.4 |
| 12 | 4.8 | 5.4 | 5.5 | NA | 3.9 | 5.0 | 5.4 | 5.2 |
| 13 | ND | ND | ND | NA | ND | ND | ND | ND |
| 14 | 7.6 | 7.7 | 8.7 | NA | 8.4 | 7.8 | 9.8 | 9.5 |
| 15 | 19.5 | 16.8 | 16.8 | NA | 20.3 | 23.8 | 18.3 | 17.7 |
| 16 | 9.6 | 10.7 | 11.0 | NA | 9.2 | 10.4 | 12.1 | 10.4 |
| 17 | 9.1 | 11.0 | 11.1 | NA | 7.3 | 9.2 | 9.9 | 10.4 |
| 18 | ND | ND | ND | NA | ND | ND | ND | ND |

B. N-Terminal. Amino Acid Sequence

The procedures used for N-terminal amino acid sequence analyses are similar to those previously described. [Edman, *Acta Chem. Scant.* 4:283 (1950); Edman et al. *Eur. J. Boochem,* 1:80 (1967)].

For each RP-HPLC peak, approximately 500 pmoles of protein were loaded on a pre-cycled filter and sequenced for 30–35 cycles. The sequencing was performed on an Applied Biosystems ABI-470A sequencer equipped with an on-line phenylhydantion (PTH) amino acid analyzer. The sequencing procedure in this instrument is based on Edman degradation.

N-terminal sequencing based on Edman degradation is very effective in identifying and quantitating residues in relatively short peptide sequences (i.e. <20). However, for long peptide sequences (i.e. >30) the identification of residues closer to the C-terminus of the protein or polypeptide becomes ambiguous. This increase in ambiguity is due to the repetitive yield, which is generally less than 95% and therefore, leads to a cumulative loss of signal for each additional cycle.

For this reason, proteins in peaks 1a and 1b were cleaved by hydrolysis at methionine residues with CNBr in order to confirm that they were IFN-α2 subspecies. The cleavage was performed by first dissolving the alpha interferon protein in 70% formic acid and then adding CNBr to a concentration of 1M and incubating at 4° C. for 24 hours. The cleavage reaction was terminated by lyophilization in a speed-vac, thus removing all solvents including CNBr from the reaction tube. The dried CNBr fragments were dissolved in 10% TFA and injected to a C18 column (0.2×25 cm, Phenomenex). Elution of the fragments was accomplished by a multi-step gradient of 0.1% TFA/H₂O (solvent A) and 0.1% TFA/acetonitrile (solvent B) at a flow rate of 0.2 ml/min. The multi-step linear gradients used are as follows: 1) 0% to 40% solvent B in 60 minutes, 2) 40% to 60% solvent B in 50 minutes, 3) 60% to 100% solvent B in 13 minutes, and 4) constant 100% solvent B for an additional 5 minutes. Detection of the eluting fragments was accomplished by monitoring absorbance at 214 nm. The resolved fragments were sequenced as indicated above.

This cleavage procedure resulted in six fragments which were resolved by RP-HPLC. A peak eluting at 75–80 minutes was sequenced and found to contain two sequences. One sequence could be aligned with that of CNBr fragment #2 composed of amino acids from position 22 to position 59 of IFN-α2b; while the second sequence aligned with that of the CNBr fragment #5 composed of amino acids from position 112 to position 148 of IFN-α2b.

Results

The N-terminal sequences for unfractionated IFN α-n3a and the fractionated RP-HPLC peaks are presented in Table 10. The results shows that unfractionated alpha interferon as well as individual peaks contain multiple sequences. All of these sequences are identified as human alpha interferon species. The major sequences in each peak are shown in Table 11.

TABLE 10

N-Terminal Sequence of IFN α-n3a and RP-HPLC Peaks

| Cycle # | IFN α-n3a | Peak 1a | Peak 1b | Peak 2 | Peak 3 |
|---|---|---|---|---|---|
| 1 | ND*(Cys) | ND | ND | ND | ND |
| 2 | Asp | Asp | Asp | Asp | Asp |
| 3 | Leu | Leu | Leu | Leu | Leu |
| 4 | Pro | Pro | Pro | Pro | Pro |
| 5 | Gln | Gln | Gln | Gln | Gln |
| 6 | Thr | Thr | Thr | Thr | Thr |
| 7 | His | His | His | His | His |
| 8 | Ser | Ser | Ser | Ser | Ser |
| 9 | Leu | Leu | Leu | Leu | Leu |
| 10 | Gly | Gly | Gly | Gly | Gly |
| 11 | Asn, Ser | Ser | Ser | Asn, Ser | Asn |
| 12 | Arg | Arg | Arg | Arg | Arg |
| 13 | Arg | Arg | Arg | Arg | Arg |
| 14 | Ala, Thr | Thr | Thr | Ala | Ala |
| 15 | Leu | Leu | Leu | Leu | Leu |
| 16 | Ile, Met | Met | Met | Ile | Ile |
| 17 | Leu | Leu | Leu | Leu | Leu |
| 18 | Leu | Leu | Leu | Leu | Leu |
| 19 | Ala, Gly | Ala | Ala | Ala | Gly |
| 20 | Gln | Gln | Gln | Gln | Gln |
| 21 | Met | Met | Met | Met | Met |
| 22 | Arg, Gly | Arg | Arg | Gly, Arg | Gly |
| 23 | Arg | Arg | Arg | Arg | Arg |
| 24 | Ile | Ile | Ile | Ile | ND |
| 25 | Ser | Ser | ND | Ser | ND |
| 26 | Pro | Leu | Leu | His | ND |
| 27 | Phe, Pro | Pro | Pro | Phe | ND |
| 28 | Ser | ND | Ser | Ser | ND |
| 29 | ND (Cys) | ND | ND | ND | ND |
| 30 | ND | Leu | Leu | Leu | ND |
| 31 | ND | ND | Lys | ND | ND |
| 32 | Asp | Asp | Asp | Asp | ND |
| 33 | Arg | Arg | Arg | Arg | ND |
| 34 | His | His | His | His | ND |
| SEQUENCE ID NO: | 5 | 6 | 7 | 8 | 9 |

| Cycle # | Peak 4 | Peak 5 | Peak 6 |
|---|---|---|---|
| 1 | ND* | ND | ND |
| 2 | Asp | Asp | Asp |
| 3 | Leu | Leu | Leu |
| 4 | Pro | Pro | Pro |
| 5 | Gln | Gln | Gln |
| 6 | Thr | Thr | Thr |
| 7 | His | His | His |
| 8 | Ser | Ser | Ser |
| 9 | Leu | Leu | Leu |
| 10 | Gly | Gly, Arg | Gly |
| 11 | Asn | Asn | Asn |
| 12 | Arg | Arg | Arg |
| 13 | Arg | Arg | Arg |
| 14 | Ala | Ala | Ala |
| 15 | Leu | Leu | Leu |
| 16 | Ile | Ile | Ile |
| 17 | Leu | Leu | Leu |
| 18 | Leu | Leu | Leu |
| 19 | Ala | Ala | Ala |
| 20 | Gln | Gln | ND |
| 21 | Met | Met | Met |
| 22 | Arg, Gly | Gly | Arg |
| 23 | Arg | Arg | Arg |
| 24 | Ile | Ile | Ile |
| 25 | Ser | Ser | Ser |
| 26 | Pro | Pro | Pro |
| 27 | Phe | Phe | Phe |
| 28 | Ser | Ser | Ser |
| 29 | ND | ND | ND |
| 30 | Leu | Leu | Leu |
| 31 | Lys | ND | Lys |
| 32 | Asp | Asp | Asp |
| 33 | Arg | Arg | Arg |
| 34 | His | His | His |
| SEQUENCE ID NO: | 10 | 11 | 12 |

*ND = not determined

TABLE 11

Major Interferon Species Based on N-Terminal Sequencing

| Peak # | Major IFN-Subspecies |
|---|---|
| 1a | α2(b/c) |
| 1b | α2(b/c) |
| 2 | α4(a/b); α16 |
| 3 | α10a |
| 4 | α8(a/b/c); α21(a/b); α17(a/b/c/d) |
| 5 | α17(a/b/c/d); α21(a/b); α7(a/b/c) |
| 6 | α8(a/b/c) |

There are a total of 18 potential subspecies in IFNα-n3a as determined by the N-terminal sequencing. These sequences are consistent with the interferon subspecies recognized by NK2 monoclonal antibody as described by Celltech, Ltd. IFN-α2b and α8(a/b/c) are the major sequences determined in alpha-n3a interferon. IFN-α2b is found primarily in peaks 1a and 1b, and in minor amounts in peak 2. IFN-α2c is found in trace amounts in peak 1a. IFN-α8(a/b/c) is found primarily in peaks 4 and 6.

Other interferon subspecies presented in lesser amounts are α4(a/b) and/or α16, which are found in peak 2. Subspecies α10a is found in peak 3. Subspecies α516 is found in trace amounts in peak 2. Subspecies α17(a/b/c) and α21(a/b) are found primarily in peak 5, and in trace amounts in peak 4. Subspecies α7(a/b/c) are found primarily in peak 5. Because the sequencing analyses were carried out to 30–35 cycles, it is difficult to distinguish some of the subspecies which have sequence identity within these 30–35 cycles. The N-terminal sequences of all human interferon alpha subspecies reported show that α21(a/b) and α17(a/b/c/d) have similar N-terminal sequences (up to amino acid position 33); so do α4(a/b) and α16 (up to amino acid position 33); and α2b as compared with α2c. Therefore, some of the minor subspecies due to the limitation of the analysis can not be excluded.

The minor differences that may exist in the amino acid sequence for the individual interferon proteins may be due to alpha interferon protein species differences, or genetic allelism. The latter may result in the appearance of a similar protein with an amino acid modification at a single site.

The product was further assayed to determine which IFN-α2 subspecies are present in the interferon product. There have been three IFN-α2 subspecies reported previously, IFN-α2a, IFN-α2b and IFN-α2c. The difference in N-terminal sequences for these three IFN-α2 subspecies are at cycles 23 and 34 are illustrated in Table 12.

TABLE 12

Difference in Sequence of IFN-α2 Subspecies

| Cycle | α2a | α2b | α2c |
|---|---|---|---|
| 23 | Lys | Arg | Arg |
| 34 | His | His | Arg |

The sequencing data of both intact protein and the CNBr fragment #2 for peaks 1a and 1b up to 35 cycles (Table 9 above) shows that the IFN-α2b is the major component present in RP-HPLC peaks 1a and 1b. The PTH amino acids released at cycles 23 and 34 are arginine (Arg) and histidine (His), respectively, in agreement with the sequence expected for IFN-α2b. There is no appreciable release of lysine (Lys) at cycle 23, indicating that IFN-α2a is not present in peaks 1a and 1b, or in any of the other RP-HPLC peaks from IFN α-n3a.

These results have been verified by peptide mapping and N-terminal sequencing of peptides released following CNBr cleavage. Furthermore, to detect IFN-α2c, the CNBr fragment spanning from Arg at position 22 to Met at position 60 was isolated and cleaved with trypsin. The tryptic peptides were resolved by RP-HPLC and sequenced. Quantitation of these sequences shows that greater than 90% of IFN-α2 in IFN α-n3a is IFN-α2b. IFN-α2c may be present in the preparation, but its concentration is below reliable detection.

C. Carbohydrate Content

The interferon protein sample (150 μg) was dialyzed 2 logs against 0.1M acetic acid and its volume reduced to about 300 μl. The concentrated sample was divided into three equal aliquots and evaporated to dryness. These samples were then hydrolyzed in 1) 2M trifluoroacetic acid (TFA) at 100° C. for 4 hours for the neutral sugar determination, 2) 6 N HCl at 100° C. for 4 hours for amino sugar determination, or 3) 0.1N HCl at 80° C. for 1 hour for sialic acid determination. The hydrolysates were evaporated to dryness and the residues were reconstituted in 170 μl of HPLC quality water and briefly heated at 80°–100° C. to facilitate dissolution.

Monosaccharides, i.e. carbohydrate standards containing 2.5 μg/ml of glucose, galactose, glucosamine, galactosamine, fucose and mannose, were prepared in HPLC grade water. A Dionex® HPLC system equipped with CarboPac® PA1 anion exchange column was used for separation of monosaccharides. The Pulsed Amperometric Detector was equilibrated with 19 mM NaOH at a flow rate of 1 ml/min and then with a post column stabilizer (0.5M NaOH) at a flow rate of 0.5 ml/min for 2 hours. 90 ul of the standard or the sample were injected via automatic injector and the sugars were eluted under isocratic conditions with 19 mM NaOH.

The sialic acid standard at 2.5 ug/ml was prepared in HPLC grade water. Sialic acid was eluted in the same Dionex® HPLC system as mentioned above. The Pulsed Amperometric Detector was equilibrated with 250 mM NaOH. 90 μl standard or the sample hydrolysate was injected and eluted under isocratic conditions with 250 mM NaOH.

The carbohydrate content was calculated as the ratio of moles sugar to moles alpha interferon protein.

The data from carbohydrate analyses for amino sugars, neutral sugars and sialic acids are presented in Table 13.

TABLE 13

Carbohydrate and Sialic Acid Content in IFN α-n3a and RP-HPLC Peaks

| Peaks | GalN | GlcN | Gal | Glc | Man | Sial | Total |
|---|---|---|---|---|---|---|---|
| Unfrac. IFN | 0.39 | 0.31 | 0.48 | 0.65 | 0.20 | 0.61 | 2.64 |
| 1a | 0.49 | 0.67 | 1.51 | 0.36 | 0.00 | 0.33 | 3.36 |
| 1b | 0.41 | 0.34 | 1.15 | 0.35 | 0.07 | 0.44 | 3.26 |
| 2 | NA | NA | NA | NA | NA | NA | NA |
| 3 | 0.33 | 0.00 | 0.37 | 1.22 | 0.00 | 0.00 | 1.92 |
| 4 | 0.00* | 0.05* | 0.84 | 2.03 | 0.00 | 0.00 | 2.92 |
| 5 | 0.27 | 0.17 | 0.29 | 0.68 | 0.00 | 0.00 | 1.41 |
| 6 | 0.08 | 0.00 | 0.34 | 0.41 | 0.00 | 0.00 | 0.83 |

NA = Not Available for Analysis.
*Determined by TFA hydrolyzed sample.

The unfractionated IFN α-n3a as well as all individual peaks, contain carbohydrate which is in the range of 1–3 moles of sugar per mole of interferon. Peaks 1a and 1b, contain the most carbohydrate as compared with the later eluting peaks. Peak 6, i.e., IFN-α8(a/b/c), contains the least amount of carbohydrate. There is no detectable mannose or sialic acid in the later peaks 3 to 6. This phenomenon is consistent with the hydrophobicity of the proteins. The lower content of the carbohydrate in the protein results in the higher hydrophobicity, and thus the protein is eluted later on RP-HPLC. The proteins in Peak 2 were not analyzed due to the shortage of material in this peak.

In another experiment to determine the glycosylation site, approximately 100 μg of protein from peaks 1a and 1b were denatured, reduced and alkylated. The protein was then subjected to digestion with glutamic acid endopeptidase (V8) at a ratio of 1:100 (E:S). The resulting V8 fragments were resolved by HPLC and collected into fractions. The fractions were hydrolyzed for release of carbohydrates and subjected to carbohydrate analysis. Fractions 52–53 were found to contain the majority of the carbohydrates. Subsequently these two fractions were N-terminally sequenced.

The sequence was that of an IFN-α2 peptide with a sequence at the N-terminal region from positions 97 to about 109 of SEQ ID NO: 1, wherein the first X is probably C and the second X is probably T. This peptide is generated by a V8 cut at E96 of IFN-α2b. The lack of signal at T at position 106, while T at position 108 is clearly detected, demonstrates that T at position 106 must be modified by O-linked carbohydrates. Therefore, threonine 106 is determined as the glycosylation site for IFN α2(b/c).

D. Carboxyl Terminus Amino Acid Sequencing

Peaks 1a and 1b were analyzed using the sequencing method for the carboxyl terminus of proteins using carboxypeptidase P. Carboxypeptidase P hydrolyses the amino acids more rapidly and has almost no preference for a particular amino acid. The interferons on peaks 2–6 were not analyzed due to shortage of material.

A protein sample (10–30 μg) was dialyzed against 50 mM sodium acetate at pH 5.5. Carboxypeptidase P was added at an enzyme:protein ratio of 1:100 (w/w). The mixture was incubated at 37° C. and aliquots were taken at 0.5, 1, 2, 5, 10 and 60 minutes. Each digestion and analysis was repeated at least twice.

The liberated amino acids from each time point were derivatized with O-phataldehyde (OPA) in 2% SDS/0.4M lithium borate for 30 seconds. The derivatized amino acids were separated on a C18 reverse phase Pico-Tag column using a methanol gradient against a sodium acetate/tetrahydrofurane/water buffer. Identification and quantification of released amino acids was done by comparison to an HPLC profile of OPA derivatized standard amino acids.

The results from C-terminal sequencing analyses for IFN α-n3a RP-HPLC peaks and alpha-interferon subspecies are summarized in Table 14.

TABLE 14

C-Terminal Sequences of alpha-Interferon Species, IFN α-n3a and RP-HPLC Peaks

| Subtypes IFN-α | Cycles | | | | |
|---|---|---|---|---|---|
| | −5 | −4 | −3 | −2 | −1 |
| Concensus [SEQ ID No: 13] | Leu | Arg | Arg | Lys | Asp |
| α2(b/c) [SEQ ID NO: 14] | Leu | Arg | Ser | Lys | Glu |
| α8(a/b/c) [SEQ ID NO: 15] | Leu | Lys | Ser | Lys | Glu |
| α4(a/b) [SEQ ID | Leu | Arg | Arg | Lys | Asp |

TABLE 14-continued

C-Terminal Sequences of alpha-Interferon Species, IFN α-n3a and RP-HPLC Peaks

| Subtypes IFN-α | Cycles | | | | |
|---|---|---|---|---|---|
| | −5 | −4 | −3 | −2 | −1 |
| NO: 16] α10a [SEQ ID NO: 17] | Leu | Arg | Arg | Lys | Asp |
| α21(a/b) [SEQ ID NO: 18] | Leu | Arg | Arg | Lys | Glu |
| α7(a/b/c) [SEQ ID NO: 19] | Leu | Arg | Arg | Lys | Asp |
| IFN α-n3a [SEQ ID NO: 20] | Leu | Arg | Ser(Arg) | Lys | Glu |
| Peak 1a [SEQ ID NO: 21] | Leu | Arg | Ser | Lys | Glu |
| Peak 1b [SEQ ID NO: 22] | Leu | Arg | Ser | Lys | Glu |

The sequence was identified based on the order of appearance and plateau of the individual amino acid residues. For example glutamic acid appears and plateaus earlier than other residues, and hence it is determined as the first residue from the C-terminus. Sequences from other cycles were determined using a similar principle. In the case of unfractionated alpha interferon, the major C-terminal sequence was determined as Leu-Arg-(Ser/Arg)-Lys-Glu [SEQ ID NO: 2].

The theoretical sequences for those alpha interferon subspecies are also presented in Table 14 for comparison. The results show that the major C-terminal sequence for peaks 1a and 1b as well as the unfractionated interferon is similar to that of IFN-α2b. This demonstrates that unfractionated interferon and peaks 1a and 1b contain intact carboxyl termini. The C-terminal sequencing analysis used here is much less sensitive than the N-terminal sequencing. Any minor difference may not be detected. For instance, α8 C-terminal residues (Leu-Lys-Ser-Lys-Glu) [SEQ ID NO: 3] were not detected in the presence of major α2b C-terminal residues (Leu-Arg-Ser-Lys-Glu) [SEQ ID NO: 4], where the two sequences only differ at cycle -4. The presence of a minor interferon component with a truncated C-terminus was not detected if the amount of component is less than 20%.

EXAMPLE 7 - PHASE I TOXICITY STUDIES

A Phase 1 study of IFN α-n3a was conducted in 20 asymptomatic HIV-infected individuals with CD4+T cell counts ≧400/mm³. The composition, prior to appropriate dosage dilution, contained 5 MU/ml IFN α-n3a in 3.3 mg phenol, 1 mg albumin (human), pH 7.4, PBS, 8.0 ng/ml NaCl, 1.74 mg/ml sodium phosphate dibasic, 0.2 mg/ml potassium phosphate monobasic, and 0.2 mg/ml potassium chloride.

This composition was administered subcutaneously Mon, Wed, and Fri (3 days/week) for 3 to 6 months at the following doses: 5 persons at 1 million IU/dose, 10 persons at 2.5 million IU/dose for the first week and then 5 million IU/dose, and 5 persons escalated to their maximum tolerated dose. Patients were observed in hospital for the first week of drug treatment.

The results of this study are reported in Table 15 below. IFN α-n3a was well tolerated at doses ≦17.5 million IU. Essentially no fever or flu-like symptoms, gastrointestinal symptoms, or skin rashes were observed. Laboratory test values for total leukocyte, granulocyte, and platelet counts were all within normal limits according to WHO requirements. Surrogate markers for alpha interferon activity (increased class I MHC expression on blood leukocytes; alpha interferon-inducible gene expression) were present in most subjects.

The frequency of adverse symptoms and laboratory test abnormalities reported for recombinant alpha interferon were not observed with equivalent doses of the composition of this invention. This favorable safety and tolerance profile, combined with solid in vitro evidence for antiviral activity of the less purified product previously used in clinical studies, reported as IFN alfa-n3 [see Alferon® A package insert, Interferon Sciences, Inc., N.J.], indicates the usefulness of the composition as a potent and remarkably safe antiviral therapeutic.

TABLE 15

Treatment-related Adverse Experiences (%)
Alferon N Injection

Early HIV Infection

| Millions of Units and Regimen No. of Patients | 1 million units 3 times/week N = 5 | 2.5/5 million units 3 times/week N = 10 |
|---|---|---|
| Fever | 0 | 0 |
| Headache | 0 | 0 |
| Myalgia | 0 | 0 |
| Fatigue | 0 | 10 |
| Rigors | 0 | 0 |
| Arthralgia | 0 | 0 |
| Dizziness | 0 | 0 |
| Diarrhea | 0 | 0 |
| Anorexia | 0 | 0 |
| Nausea | 0 | 0 |
| Alopecia | 0 | 0 |

In order to demonstrate the striking advantage of low toxicity of the composition of the present invention over known alpha interferon compositions, the toxicity results are compared in Table 16 below to a number of other reported alpha interferons, both natural, cell derived and recombinant. For ease of comparison, the IFN α-n3a was compared to several alpha, as well as beta and gamma interferons individually described in the following references. In Table 16, the reference numbers refer to the following references:

1. G. M. Scott et al, *British Medical Journal*, 282:1345 (1981)
2. S. L. Sacks et al, *Antimicrobial Agents & Chemotherapy*, 21:93 (1982)
3. J. H. Schiller et al, *J. Clinical Investigation*, 86:1211 (1990)
4. S. Ingimarsson et al, *J. Infectious Disease*, 140:560 (1979)
5. H. C. Lane et al, *Annals of Internal Medicine*, 112:805 (1990)
6. R. Kurzrock et al, *J. Clinical Oncology*, 4:1101 (1986)
7. R. J. Spiegel, *Clinical Overview of α-IFN*, page 627 (1987)
8. T. Taguchi, *Cancer*, 57:1705 (1986)
9. R. M. Bukowski et al, *Cancer Research*, 51:836 (1991)
10. H. G. Klingemann et al, *Blood*, 78:3306 (1991)
11. Roferon®A, PDR 2006 (1993)
12. Intron®A, PDR 2194 (1993)
13. R. J. Wells et al, *J. Interferon Res.*, 8:309 (1988)
14. G. J. Jones et al, *Cancer*, 57:1709 (1986)
15. Alferon® N Injection, Package Insert

TABLE 16

| Reference | 1 | 1 | 2 | 3 | 3 | 3 |
|---|---|---|---|---|---|---|
| IFN Used | PIFα | NK2 IFNα | PIFα | IFN βser | IFN-βser | rIFN-γ |
| Dose | 1.3 MU/m$^2$ | 1.12 MU/m$^2$ | 2 + 20 MU/dose 1 + 2x/day | 3 MU | 30 MU | 3 MU |
| N | 9 | 9 | 38; 113 | 10 | 11 | 10 |
| FLU-LIKE SYMPTOMS: | | | | | | |
| Fever | 78 | 67 | 40 | | | |
| Fatigue | 67 | 67 | 29 | 10 | 45 | 10 |
| Myalgia | 56 | 56 | 24 | 0 | 36 | 0 |
| Headache | 100 | 89 | | 20 | 45 | 20 |
| Chills (Rigors) | 67 | 67 | | 0 | 9 | 0 |
| Malaise | 89 | 78 | 31 | | | |
| Upper Respiratory Infection | | | | | | |
| Reference | 1 | 1 | 2 | 3 | 3 | 3 |
| IFN Used | PIFα | NK2 IFNα | PIFα | IFN βser | IFN-βser | rIFN-γ |
| Dose | 1.3 MU/m$^2$ | 1.12 MU/m$^2$ | 2 + 20 MU/dose 1 + 2x/day | 3 MU | 30 MU | 3 MU |
| N | 9 | 9 | 38; 113 | 10 | 11 | 10 |
| CNS & | | | | | | |

TABLE 16-continued

| PERIPHERAL: | | | | | | |
|---|---|---|---|---|---|---|
| Depression | | | 8 | | | |
| Dizzness | | | | | | |
| Paresthesia | | | | | | |
| Numbness | | | | | | |
| Transient | | | | | | |
| Impotency | | | | | | |
| Shaking | 33 | 33 | | | | |
| Difficulty in Concentrating | | | | | | |

| Reference | 1 | 1 | 2 | 3 | 3 | 3 |
|---|---|---|---|---|---|---|
| IFN Used | PIFα | NK2 IFNα | PIFα | IFN βser | IFN-βser | rIFN-γ |
| Dose | 1.3 MU/m$^2$ | 1.12 MU/m$^2$ | 2 + 20 MU/dose 1 + 2x/day | 3 MU | 30 MU | 3 MU |
| N | 9 | 9 | 38; 113 | 10 | 11 | 10 |
| CNS & PERIPHERAL: | | | | | | |
| Insomnia | | | | | | |
| GASTRO-INTESTINAL: | | | | | | |
| Anorexia | 22 | 33 | | 0 | 18 | 0 |
| Nausea | 33 | 33 | 8 | 0 | 18 | 0 |
| Diarrhea | | | | | | |
| Emesis (Vomiting) | | | | | | |
| Dyspepsia/ Heartburn | | | | | | |

| Reference | 1 | 1 | 2 | 3 | 3 | 3 |
|---|---|---|---|---|---|---|
| IFN Used | PIFα | NK2 IFNα | PIFα | IFN βser | IFN-βser | rIFN-γ |
| Dose | 1.3 MU/m$^{22}$ | 1.12 14U/m$^2$ | 2 + 20 MU/dose 1 + 2x/day | 3 MU | 30 MU | 3 MU |
| N | 9 | 9 | 38; 113 | 10 | 11 | 10 |
| SKIN: | | | | | | |
| Rash | | | | | | |
| Dry Skin/ Pruritis | | | | | | |
| Partial Alopecia (Hair loss) | | | 21 | | | |
| HEMATOLOGY: | | | | | | |
| Leukopenia ($\times 10^3$/mm$^3$) | | | | −1.8 | −2.8 | −1.3 |
| Neutropenia ($\times 10^3$/mm$^3$) | | | | −1.6 | −1.9 | −1.5 |
| Lymph ($\times 10^3$/mm$^3$) | | | | −0.17 | −0.44 | −0.15 |

| Reference | 1 | 1 | 2 | 3 | 3 | 3 |
|---|---|---|---|---|---|---|
| IFN Used | PIFα | NK2 IFNα | PIFα | IFN βser | IFN-βser | rIFN-γ |
| Dose | 1.3 MU/m$^2$ | 1.12 MU/m$^2$ | 2 + 20 MU/dose 1 + 2x/day | 3 MU | 30 MU | 3 MU |
| N | 9 | 9 | 38; 113 | 10 | 11 | 10 |
| HEMATOLOGY: | | | | | | |
| Thrombocyto-penia ($\times 10^3$/mm$^3$) | | | | −12.3 | −7.6 | + 2.2 |
| Hematocrit/ Anemia (ml/dl) | | | | −0.1 | −1.5 | + 0.5 |
| Neutralizing Antibody | | | | | | |
| OTHER: | | | | | | |
| Anxiety | | | | | | |

TABLE 16-continued

| Reference | 1 | 1 | 2 | 3 | 3 | 3 |
|---|---|---|---|---|---|---|
| IFN Used | PIFα | NK2 IFNα | PIFα | IFN βser | IFN-βser | rIFN-γ |
| Dose | 1.3 MU/m² | 1.12 MU/m² | 2 + 20 MU/dose 1 + 2x/day | 3 MU | 30 MU | 3 MU |
| N | 9 | 9 | 38; 113 | 10 | 10 | |
| OTHER: | | | | | | |
| Dryness or Inflamation of oropharynx | | | | | | |
| Weight Loss | | | 11 | | | |
| Change in Taste | | | | | | |
| Renal Toxicity | | | | | | |
| Reactivation of Herpes Genitalis | | | | | | |
| Lower Back Pain | 56 | 44 | | | | |

| Reference | 1 | 1 | 2 | 3 | 3 | 3 |
|---|---|---|---|---|---|---|
| IFN Used | PIFα | NK2 IFNα | PIFα | N βser | IFN-βser | rIFN-γ |
| Dose | 1.3 MU/m²² | 1.12 MU/m² | 2 + 20 MU/dose 1 + 2x/day | 3 MU | 30 MU | 3 MU |
| N | 9 | 9 | 38; 113 | 10 | 11 | 10 |
| OTHER: | | | | | | |
| Joint Pain/ Arthralgia | 33 | 56 | | | | |
| Liver Toxicity | | | | | | |
| Local Pain | | | | | | |
| Coryza | | | | | | |
| Feebleness | | | | | | |
| Perspiration/ Sweating/ Diaphoresis | | | | | | |
| Stiffness | | | | | | |

| Reference | 4 | 5 | 6 | 7 | 8 | 9 |
|---|---|---|---|---|---|---|
| IFN Used | CIFα PIFα | rIFN-α2b | rIFN-γ | rIFN-α2b | rIFN-FNα2a | Natural IFN-β |
| Dose | 3 MU/d | 35 MU/d | 20 MU/m²/d | Variable | 36 MU | |
| N | 29 | 11 | ? | ? | 4 | 34 |
| FLU-LIKE SYMPTOMS: | 75 | | | | | |
| Fever | 62 | 100 | 100 | 98 | 100 | |
| Fatigue | | 100 | 100 | 98 | 50 | |
| Myalgia | | 100 | 100 | 98 | | |
| Headache | 10 | 100 | 84 | 98 | 25 | |
| Chills (Rigors) | 38 | 100 | 70 | 98 | 50 | |
| Malaise | | 100 | | 98 | | |
| Upper Respiratory Infection | | 73 | | | | |

| Reference | 4 | 5 | 6 | 7 | 8 | 9 |
|---|---|---|---|---|---|---|
| IFN Used | CIFα PIFα | rIFN-α2b | rIFN-γ | rIFN-α2b | rIFN-FNα2a | Natural IFN-β |
| Dose | 3 MU/d | 35 MU/d | 20 MU/m²/d | variable | 36 MU | |
| N | 29 | 11 | ? | ? | 4 | 34 |
| CNS & PERIPHERAL: | | | | | | |
| Depression | | 27 | | | | |
| Dizziness | | | | 34 | | |
| Paresthesia | | | | 34 | | |
| Numbness | | | | 34 | | |
| Transient Impotency | | | | 34 | | |
| Shaking | | | | 34 | | |
| Difficulty | | 45 | 0 | | | |

TABLE 16-continued

| | | | | | | |
|---|---|---|---|---|---|---|
| in Concentrating | | | | | | |
| Reference | 4 | 5 | 6 | 7 | 8 | 9 |
| IFN Used | CIFα PIFα | rIFN-α2b | rIFN-γ | rIFN-α2b | rIFN-FNα2a | Natural IFN-β |
| Dose | 3 MU/d | 35 MU/d | 20 MU/m$^{2/d}$ | Variable | 36 MU | |
| N | 29 | 11 | ? | ? | 4 | 34 |
| CNS & PERIPHERAL: | | | | | | |
| Insomnia | | | | | | 44 |
| GASTRO-INTESTINAL: | | | | | | |
| Anorexia | | 27 | | 27 | 25 | |
| Nausea | | | 36 | 50 | 75 | |
| Diarrhea | | 73 | 7 | 27 | | |
| Emesis (Vomiting) | | | | 27 | | |
| Dypepsia/ Heartburn | | | | | | |

| | | | | | | |
|---|---|---|---|---|---|---|
| Reference | 4 | 5 | 6 | 7 | 8 | 9 |
| IFN Used | CIFα PIFα | rIFN-α2b | rIFN-γ | rIFN-α2b | rIFN-FNα2a | Natural IFN-β |
| Dose | 3 MU/d | 35 MU/d | 20 MU/m$^2$/d | Variable | 36 MU | |
| N | 29 | 11 | ? | ? | 4 | 34 |
| SKIN: | | | | | | |
| Rash | | 27 | | 12 | | |
| Dry Skin/ Pruritis | 17 | | | 12 | | |
| Partial Alopecia (Hair loss) | 28 | 45 | | 4 | | |
| HEMATOLOGY: | | | | | | |
| Leukopenia (× 10$^3$/mm$^3$) | | | | 75% | | |
| Neutropenia (× 10$^3$/mm$^3$) | | 55 | | 25 | 9% | |
| Lymphopenia (× 10$^3$/mm$^3$) | | | | | | |

| | | | | | | |
|---|---|---|---|---|---|---|
| Reference | 4 | 5 | 6 | 7 | 8 | 9 |
| IFN Used | CIFα PIFα | rIFN-α2b | rIFN-γ | rIFN-α2b | rIFN-FNα2a | Natural IFN-β |
| Dose | 3 MU/d | 35 MU/d | 20 MU/m$^2$/d | Variable | 36 MU | |
| N | 29 | 11 | ? | ? | 4 | 34 |
| HEMATOLOGY: | | | | | | |
| Thrombocytopenia (× 10$^3$/mm$^3$) | | | | 25% | | |
| Hematocrit/ Anemia (ml/dl) | | | | | 38% | |
| Neutralizing Antibody | | | 0 | | | |
| OTHER: | | | | | | |
| Anxiety | | 27 | | | | |

| | | | | | | |
|---|---|---|---|---|---|---|
| Reference | 4 | 5 | 6 | 7 | 8 | 9 |
| IFN Used | CIFα PIFα | rIFN-α2b | rIFN-γ | rIFN-α2b | rIFN-FNα2a | Natural IFN-β |
| Dose | 3 MU/d | 35 MU/d | 20 MU/m$^2$/d | variable | 36 MU | |
| N | 29 | 11 | ? | ? | 4 | 34 |
| OTHER: | | | | | | |
| Dryness or Inflamation of Oropharynx | | | | | | |
| Weight Loss | | | | 4 | | |
| Change in | | | | | | |

TABLE 16-continued

| | | | | | | |
|---|---|---|---|---|---|---|
| Taste | | | | | | |
| Renal Toxicity | | 27 | 42 | | | |
| Reactivation of Herpes Genitalis | | | | | | |
| Lower Back Pain | | | | | | |

| Reference | 4 | 5 | 6 | 7 | 8 | 9 |
|---|---|---|---|---|---|---|
| IFN Used | CIFα PIFα | rIFN-α2b | rIFN-γ | rIFN-α2b | rIFN-FNα2a | Natural IFN-β |
| Dose | 3 MU/d | 35 MU/d | 20 MU/m$^2$/d | variable | 36 MU | |
| N | 29 | 11 | ? | ? | 4 | 34 |
| OTHER: | | | | | | |
| Joint Pain/ Arthralgia | | | | | | |
| Liver Toxicity | | 45 | 91 | | 32 | |
| Local Pain | 38 | | | | | |
| Coryza | 14 | | | | | |
| Feebleness | 10 | | | | | |
| Perspiration/ Sweating/ Diaphoresis | 10 | | | | | |
| Stiffness | 10 | | | | | |

| Reference | 10 | 11 | 12 | 13 | 14 | 15 |
|---|---|---|---|---|---|---|
| IFN Used | rIFN-α2b | rIFN-α2a | rIFN-α2b | IFN-αn1 | rIFN-α2a | IFN-αn3 |
| Dose | 1.5 MU/m$^2$ | 3 MU/d | 2 MU/m$^2$ | Variable 2.5–15 MU/1/22 | Variable 3–72 MU | 1.25 MU/Inj |
| N | 4 | ? | 145 37 | 12 | 1019 | 104 |
| FLU-LIKE SYMPTOMS: | | | | | | |
| Fever | 0 | 98 | 68 | 83 | 86 | 40 |
| Fatigue | 75 | 89 | 61 | 25 | 90 | 14 |
| Nyalgia | 0 | 73 | 39 | | 57 | 45 |
| Headache | 0 | 71 | 39 | | 46 | 31 |
| Chills (Rigors) | | 64 | 46 | 83 | 62 | 14 |
| Malaise | | | | | | 9 |
| Upper Respiratory Infection | | | | | | |

| Reference | 10 | 11 | 12 | 13 | 14 | 15 |
|---|---|---|---|---|---|---|
| IFN Used | rIFN-α2b | rIFN-α2a | rIFN-α2b | IFN-αn1 | rIFN-α2a | IFN-αn3 |
| Dose | 1.5 MU/m$^2$ | 3 MU/d | 2 MU/m$^2$ | Variable 2.5–15 MU/m$^2$ | Variable 3–72 MU | 1.25 MU/Inj |
| N | 4 | ? | 145 | 12 | 1019 | 104 |
| CNS & PERIPHERAL: | | | | | | |
| Depression | | 23 | 6 | | 6.5 | 2 |
| Dizziness | | 21 | 12 | | | 9 |
| Paresthesia | | 6 | 6 | | 7 | |
| Numbness | | 6 | | | | |
| Transient Impotency | | 6 | | | | |
| Shaking | | <3 | | | | |
| Difficulty in Concentrating | | <3 | <5 | | 12 | |

| Reference | 10 | 11 | 12 | 13 | 14 | 15 |
|---|---|---|---|---|---|---|
| IFN Used | rIFN-α2b | rIFN-α2a | rIFN-α2b | IFN-αn1 | rIFN-α2a | IFN-αn3 |
| Dose | 1.5 MU/m$^2$ | 3 MU/d | 2 MU/m$^2$ | Variable 2.5–15 MU/m$^2$ | Variable 3–72 MU | 1.25 MU/Inj |
| N | 4 | ? | 145 | 1 2 | 1019 | 104 |
| CNS & | | | | | | |

TABLE 16-continued

| PERIPHERAL: | | | | | | |
|---|---|---|---|---|---|---|
| Insomnia | | | | | | 2 |
| GASTRO-INTESTINAL: | | | | | | |
| Anorexia | 50 | | 19 | | 68 | |
| Nausea | 25 | | 21 | 58 | 53 | 4 |
| Diarrhea | | | 18 | | 34 | 2 |
| Emesis (Vomiting) | | | 6 | | 30 | 3 |
| Dyspepsia/ Heartburn | | | | | | 3 |

| Reference | 10 | 11 | 12 | 13 | 14 | 15 |
|---|---|---|---|---|---|---|
| IFN Used | rIFN-α2b | rIFN-α2a | rIFN-α2b | IFN-αn1 | rIFN-α2a | IFN-αn3 |
| Dose | 1.5 MU/m² | 3 MU/d | 2 MU/m² | Variable 2.5–15 MU/m² | Variable 3–72 MU | 1.25 MU/Inj |
| N | 4 | ? | 145 | 12 | 1019 | 104 |
| SKIN: | 0 | | | | | |
| Rash | | 18 | | | 7 | |
| Dry Skin/ Pruritis | | 13 | | | | 2 |
| Partial Alopecia (Hair loss) | | 8 | | | 10 | |
| HEMATOLOGY: | | | | | | |
| Leukopenia (× 10³/mm³) | 50% | | | | | |
| Neutropenia (× 10³/mm³) | | | | | | |
| Lymphopenia (× 10³/mm³) | | | | | | |

| Reference | 10 | 11 | 12 | 13 | 14 | 15 |
|---|---|---|---|---|---|---|
| IFN Used | rIFN-α2b | rIFN-α2a | rIFN-α2b | IFN-αn1 | rIFN-α2a | IFN-αn3 |
| Dose | 1.5 MU/m² | 3 MU/d | 2 MU/m | Variable 2.5–15 MU/m² | Variable 3–72 MU | 1.25 MU/Inj |
| N | 4 | ? | 145 | ? | 1019 | |
| HEMATOLOGY: | | | | | | |
| Thrombocytopenia (× 10³/mm³) | 75% | | | | | |
| Hematocrit/ Anemia (ml/dl) | 75% | | | | | |
| Neutralizing Antibody | | | | | 27.4 | |
| OTHER: | | | | | | |
| Anxiety | | | | | | |

| Reference | 10 | 11 | 12 | 13 | 14 | 15 |
|---|---|---|---|---|---|---|
| IFN Used | rIFN-α2b | rIFN-α2a | rIFN-α2b | IFN-αn1 | rIFN-α2a | IFN-αn3 |
| Dose | 1.5 MU/m² | 3 MU/d | 2 MU/m² | Variable 2.5–15 MU/m² | Variable 3–72 MU | 1.25 MU/Inj |
| | 4 | ? | 145 | 12 | 1019 | 104 |
| OTHER: | | | | | | |
| Dryness or Inflamation of Oropharynx | | 16 | | | 5 | |
| Weight Loss | 50 | 14 | | | 13 | |
| Change in Taste | | 13 | | | | |
| Renal Toxicity | 0 | | | | | |
| Reactivation of Herpes Genitalis | | 8 | | | 5 | |
| Lower Back | | 19 | | | 4 | |

TABLE 16-continued

| Pain | | | | | | |
|---|---|---|---|---|---|---|
| Reference | 10 | 11 | 12 | 13 | 14 | 15 |
| IFN Used | rIFN-α2b | rIFN-α2a | rIFN-α2b | IFN-αn1 | rIFN-α2a | FN-αn3 |
| Dose | 1.5 MU/m$^2$ | 3 MU/d | 2 MU/m$^2$ | Variable 2.5–15 MU/m$^2$ | Variable 3–72 MU | 1.25 MU/Inj |
| N | 4 | ? | 145 | 12 | 1019 | 104 |
| OTHER: | | | | | | |
| Joint Pain/ Arthralgia | | 5 | 8 | | 12 | 5 |
| Liver Toxicity | 75 | | | 25 | | |
| Local Pain | | | | 44 | | |
| Coryza | | | | | | |
| Feebleness | | | | | | |
| Perspiration/ Sweating/ Diaphoresis | | 8 | 8 | | | 2 |
| Stiffness | | | | | | |

| Reference | 16 | 17 | 18 | 19 |
|---|---|---|---|---|
| IFN Used | IFN-αn3a | rIFN-α2a | rIFN-γ | rIFN-α2c |
| Dose | 1–5 MU/Inj | 8–18 MU/Inj | 1 MU/m$^2$ | –2 MU/Inj |
| N | 15 | 15 | 16 | 21 |
| FLU-LIKE SYMPTOMS: | | | | |
| Fever | 0% | 33 | 19 | >50 |
| Fatigue | <10% | 41 | 6 | 27 |
| Myalgia | <10% | 13 | 6 | |
| Headache | <10% | | 19 | 14 |
| Chills (Rigors) | 0% | 0 | | |
| Malaise | <10% | | 6 | 0 |
| Upper Respiratory Infection | 0% | | | |

| Reference | 16 | 17 | 18 | 19 |
|---|---|---|---|---|
| IFN Used | IFN-αn3a | rIFN-α2a | rIFN-γ | rIFN-α2c |
| Dose | 1–5 MU/Inj | 8–18 MU/Inj | 1 MU/m$^2$ | –2 MU/Inj |
| N | 15 | 15 | 16 | 21 |
| CNS & PERIPHERAL: | | 26 | | |
| Depression | | | | |
| Dizziness | 0% | | | |
| Paresthesia | 0% | | | |
| Numbness | 0% | | | |
| Transient Impotency | <10% | | | |
| Shaking | 0% | | | |
| Difficulty in Concentrating | <10% | | | |

| Reference | 16 | 17 | 18 | 19 |
|---|---|---|---|---|
| IFN Used | IFN-αn3a | rIFN-α2a | rIFN-γ | rIFN-α2c |
| Dose | 1–5 MU/Inj | 8–18 MU/Inj | 1 MU/m$^2$ | –2 MU/Inj |
| N | 15 | 15 | 16 | 21 |
| CNS & PERIPHERAL: | | | | |
| Insomnia | 0% | | | |
| GASTRO-INTESTINAL: | | | | |
| Anorexia | 0% | 6 | | |
| Nausea | 0% | 13 | 13 | 0 |
| Diarrhea | 0% | 0 | | |
| Emesis (Vomiting) | 0% | | 13 | |
| Dyspepsia/ | 0% | | | |

TABLE 16-continued

| Heartburn | | | | |
|---|---|---|---|---|
| Reference | 16 | 17 | 18 | 19 |
| IFN Used | IFN-αn3a | rIFN-α2a | rIFN-γ | rIFN-α2c |
| Dose | 1–5 MU/Inj | 8–18 MU/Inj | 1 MU/m$^2$ | –2 MU/Inj |
| N | 15 | 15 | 16 | 21 |
| SKIN: | | | | |
| Rash | <10% | | | 18 |
| Dry Skin/ Pruritis | <10% | | | |
| Partial Alopecia (Hair loss) | 0% | | | |
| HEMATOLOGY: | | | | |
| Leukopenia (× 10$^3$/mm$^3$) | 0% | | 13% | |
| Neutropenia (× 10$^3$/mm$^3$) | 0% | | | |
| Lymphopenia (× 10$^3$/mm$^3$) | 0% | | | |

| Reference | 16 | 17 | 18 | 19 |
|---|---|---|---|---|
| IFN Used | IFN-αn3a | rIFN-α2a | rIFN-γ | rIFN-α2c |
| Dose | 1–5 MU/Inj | 8–18 MU/Inj | 1 MU/m$^2$ | –2 MU/Inj |
| N | 15 | 15 | 16 | 21 |
| HEMATOLOGY: | | | | |
| Thrombocyto-penia (× 10$^3$/mm$^3$) | 0% | | | |
| Hematocrit/ Anemia (ml/dl) | 0% | | | |
| Neutralizing Antibody | | | | |
| OTHER: | | | | |
| Anxiety | <10% | | | |

| Reference | 16 | 17 | 18 | 19 |
|---|---|---|---|---|
| IFN Used | IFN-αn3a | rIFN-α2a | rIFN-γ | rIFN-α2c |
| Dose | 1–5 MU/Inj | 8–18 MU/Inj | 1 MU/m$^2$ | –2 MU/Inj |
| N | 15 | 15 | 16 | 21 |
| OTHER: | | | | |
| Dryness or Inflamation of oropharynx | 0% | | | |
| Weight Loss | 0% | | | |
| Change in Taste | 0% | | | |
| Renal Toxicity | 0% | | | |
| Reactivation of Herpes Genitalis | 0% | | | |
| Lower Back Pain | 0% | | | |

| Reference | 16 | 17 | 18 | 19 |
|---|---|---|---|---|
| IFN Used | IFN-αn3a | rIFN-α2a | rIFN-γ | rIFN-α2c |
| Dose | 1–5 MU/Inj | 8–18 MU/Inj | 1 MU/m$^2$ | –2 MU/Inj |
| N | 15 | 15 | 16 | 21 |
| OTHER: | | | | |
| Joint Pain/ Arthralgia | <10% | | | |
| Liver Toxicity | <10% | | | |
| Local Pain | 0% | | | |
| Coryza | 0% | | | |
| Feebleness | 0% | | | |
| Perspiration/ | 0% | | | |

TABLE 16-continued

| | |
|---|---|
| Sweating/ | |
| Diaphoresis | |
| Stiffness | 0% |

EXAMPLE 8 - ANTI-HIV-1 ACTIVITY OF INTERFERON α-n3a

Interferons are known to have antiviral effects, both in vivo and in vitro. The interferon species in IFN α-n3a were examined for their antiviral activity against Human Immunodeficiency Virus 1 (HIV-1) in a series of in vitro assays. The relative activity of IFN α-n3a was compared with two recombinant forms of alpha interferon (i.e., IFN α-2a and IFN α-2b).

A. Cell Culture and Reverse Transcriptase Assays

The cells used in these studies were normal human monocytes recovered from peripheral blood mononuclear cells (PBMC) of HIV and hepatitis B sero negative donors after leukaphoresis and purified by counter current centrifugal elutriation of mononuclear leukocyte-rich fractions of blood cells. The cell suspensions were assayed and found to be >98% monocytes and were cultured as adherent monolayers (1.5× $10^5$ cells/ml) in DMEM (Gibco, Grand Island, N.Y.) with 10% heat-inactivated A+ human serum, 50 µg/ml gentamycin, and 1000 U/ml highly purified recombinant M-CSF (FAP-809, Cetus Corp., Emeryville, Calif.). All culture reagents were tested and found to be negative for endotoxin contamination.

The adherent monocytes were cultured for 7 days in the absence of interferon, and prior to the addition of a monocyte tropic HIV-1 strain (ADA). The infected cells were incubated for up to four (4) weeks of culture in the presence or absence of added interferon. Culture medium was half-exchanged every 2 to 3 days.

The interferon used in these experiments, were of different sources and hence were first titered against another virus, i.e., Vesicular Stomatitis Virus (VSV) in a CPE assay using MDBK cells. The interferons were normalized in this CPE assay, to the same number of antiviral units/ml of culture for these experiments. When IFN is added at the same time as the virus, or just before, there is a dose dependent inhibition of HIV production by the interferon.

Reverse transcriptase (RT) activity in replicate cell cultures, and associated with the HIV-1 virus was used to quantitate the levels of viral expression in these experiments. Tissue culture fluids, collected at different times, were added to a reaction mixture consisting of 0.05% Nonidet P-40 (Sigma Chemical Co.), 10 µg/ml poly (A), 0.25 U/ml oligo (dT; Pharmacia, Piscataway, N.J.), 5 mM dithiothreitol (Pharmacia), 150 mM KCl, 15 mM $MgCl_2$ and $^3$H-dTTP (2 Ci/mmol, Amersham Corp., Arlington Heights, Ill.) in pH 7.9 TRIS-HCl buffer for 24 hours at 37° C. Incorporated radioactivity was precipitated with cold TCA, washed and collected in an automatic cell harvester (Skatron, Inc., Sterling, Va.) on glass filter disks. Radioactivity was measured in a liquid scintillation counter.

B. Comparative Effects of Interferons on HIV-1$_{ADA}$ Infection in Monocyte Cultures The dose dependent effects of IFN α-n3a were examined in vitro with HIV-1 infected monocytes, in comparison to two other available sources of IFN, i.e., recombinant IFN α-2a (Roferon® A, Hoffman-La Roche, Nutley, N.J.) and recombinant IFN α-2b (Intron® A, Schering Plough, Kenilworth, N.J.). Increasing doses of IFN (i.e., 0 to 500 IU/ml) were added to monocytes infected with HIV-1$_{ADA}$ (MOI= 0.01) and incubated for 12 days. The results, presented below in Table 17, are the average of triplicate determinations, show that IFN α-n3a is more potent, unit for unit, in the HIV-1 monocyte inhibition assay, than the two recombinant IFNs tested.

TABLE 17

| | RTase Activity (CPM × $10^{-5}$) as a Function of IFN Concentration | | | | | | |
|---|---|---|---|---|---|---|---|
| | IFN (IU/ml) | | | | | | |
| IFN Used | 0.1 | 1 | 5 | 10 | 50 | 100 | 500 |
| IFN α-2a | 253 | 300 | 355 | 327 | 212 | 60 | 50 |
| IFN α2b | 253 | 286 | 226 | 180 | 88 | 42 | 32 |
| IFN α-n3a | 253 | 230 | 138 | 58 | 58 | 21 | 18 |

**$ID_{50}$ 50% Inhibitory Dose

These assays were repeated many times to confirm these results. The summarized results are presented in Table 18 below.

TABLE 18

| Relative Inhibitory Effects of Different Forms of IFN | | |
|---|---|---|
| IFN Used | Number of Experiments | $ID_{50}$ (+ SEM) |
| IFN α-2a | 2 | 95.0 (25.0) |
| IFN α-2b | 8 | 13.7 (1.1) |
| IFN α-n3a | 6 | 1.2 (0.2) |

From these results, it was observed that the IFN α-n3a was 10 times more potent than IFN α-2b and about 100 times more potent than IFN α-2a, in this assay. This is even after normalizing the relative interferon concentrations in each preparation to the same titer, as determined in the CPE assay as described above.

C. Analyses of Anti-HIV-1 Activity in IFN α-n3a

The source of the higher anti-HIV-1 activity of IFN α-n3a in the monocyte culture assays was examined using the reverse phase HPLC fractionated peaks of IFN α-n3a. IFN α-n3a was fractionated on a RP-HPLC column as described previously and each RP-HPLC peak of IFN activity was normalized for its antiviral (i.e., VSV) CPE activity in MDBK cells prior to use in these experiments. Six peak regions were examined in these studies (i.e., peaks 1 [a+b], 2, 3, 4, 5, and 6) after normalization of CPE titer. One hundred (100) IU/ml and HIV-1 moi of ≦0.02 were used for each of the assays. The results are presented in Table 19 below.

TABLE 19

| Relative Anti-HIV-1 Activity of RP-HPLC Peaks of IFN α-n3a | | | | | | | |
|---|---|---|---|---|---|---|---|
| IFN Added (100 IU/ml) | None | Peak 1 (a + b) | Peak 2 | Peak 3 | Peak 4 | Peak 5 | Peak 6 |
| HIV-1 Activity | 0% | 26% | 95% | 75% | 87% | 88% | 98% |

TABLE 19-continued

Relative Anti-HIV-1 Activity of RP-HPLC Peaks of IFN α-n3a

| IFN Added (100 IU/ml) | None | Peak 1 (a + b) | Peak 2 | Peak 3 | Peak 4 | Peak 5 | Peak 6 |
|---|---|---|---|---|---|---|---|
| Inhibited | | | | | | | |

These results show that the majority of the anti-HIV-1 activity appears to reside in the IFN species found in RP-HPLC peaks 2 and 6, with peaks 3, 4 and 5 having strong but lesser activities. Interestingly, and unexpected was the finding that the IFN species in RP-HPLC peak 1 had the least anti-retroviral activity of the species found in IFN α-n3a. The IFN species found in this peak are IFN α2(b/c). This confirms the low anti-HIV-1 activity found for both IFN α-2a and IFN α-2b, presented above.

While certain embodiments of the invention have been particularly described, it will be apparent to those skilled in the art that many modifications and variations may be made. Therefore, the present invention is not to be construed as limited by any of the particular embodiments shown, rather its scope will be defined only by the claims which follow.

We claim:

1. A natural alpha interferon composition produced from human peripheral blood leukocytes, said composition exhibiting a substantially reduced toxicity upon administration to humans and consisting of at least 50% of alleles of α2 and α8, and one or more additional alpha interferon species and alleles thereof selected from the group consisting of α4, α7, µ10, α116, α17 and α21, said composition characterized by (a) a carbohydrate content of between 1 and 6 moles of sugar per mole of interferon protein;

(b) a specific activity range of between about $1 \times 10^8$ IU/mg and about $10 \times 10^8$ IU/mg when measured in an in vitro antiviral assay using human and bovine cells, and an average specific activity. of $4 \times 10^8$ IU/mg;

(c) a mixture of apparent molecular weights of between 16,000 and 27,000 daltons;

(d) the SDS-PAGE profiles shown in FIGS. 6 and 7;

(e) apparent isoelectric points between 5.0 and 7.5;

(f) a mixture of hydrophobicities measured by eluting in 0.1% trifluoroacetic acid from a semi-preparative C4 hydrocarbon reverse phase high pressure liquid chromatography fractionation column between 40–60% acetonitrile solvent concentration, resulting in an $OD_{280}$ profile shown in FIG. 4;

(g) the N-terminal sequences of SEQ ID NOS 5 through 12; and (h) the C-terminal sequences of SEQ ID NOS 13 through 22.

2. The composition according to claim 1 wherein said specific activity is about $4 \times 10^8$ IU/mg on human HEp-2 cells.

3. The composition according to claim 1 characterized by a purity of at least 95% human alpha interferon proteins.

4. The composition according to claim 3 wherein said purity is at least 98%.

5. The composition according to claim 3 wherein said purity is at least 99%.

6. A pharmaceutical composition comprising the alpha interferon composition according to any of claims 1–5 and a pharmaceutically acceptable carrier.

7. A method for producing the alpha interferon composition according to claim 1, comprising a mixture of alpha interferon subtypes produced from peripheral blood leukocytes comprising the following steps:

(a) preparing human peripheral blood leukocytes by collecting buffy coats and lysing red blood cells with ammonium chloride;

(b) suspending leukocytes at a cell density of $1-10 \times 10^6$ cells/ml in an induction medium, comprising Eagle's MEM containing Earle's Salts, L-glutamine, non-essential amino acids, 4.46 mg/ml Tricine, pH 7.4, 24 µg/ml neomycin sulfate, vitamins B3 and/or C, sodium bicarbonate, and between 0.1 to 1.5 mg/ml human agamma serum;

(c) adding crude or purified alpha interferon as a primer to the leukocytes suspended in the induction medium;

(d) incubating the suspension for a sufficient time at about 36° C. while stirring at 100–300 rpm;

(e) adding between 50–500 hemagglutinin units per ml of Sendai virus to the suspension;

(f) incubating for a sufficient time at about 36° C. while stirring at 100–300 rpm;

(h) centrifuging at about 2,500 rpm to remove cells and debris; and (i) collecting crude alpha interferon as product, without ever separating one alpha interferon subtype from the other subtypes present in the alpha mixture.

8. The method according to claim 7, further including the step of diluting the leukocyte suspension, after step (f), to a final concentration of about $1-5 \times 10^6$ cell/ml with the induction medium.

9. A method of purifying the crude alpha interferon produced according to either of claims 7 or 8, comprising the steps of (a) concentrating the crude interferon mixture 10 to 100 fold by filtration;

b) removing substantially all of the impurities from the crude interferon using antibody immunoaffinity chromatography with the monoclonal antibody NK2;

(c) incubating the affinity purified interferon in acid for at least 2 days at 4° C.; and (d) further purifying the affinity purified interferon by gel filtration chromatography.

10. A pharmaceutical composition comprising the alpha interferon composition according to claim 1 and a pharmaceutically acceptable carrier, characterized by a substantially reduced toxicity upon administration as an antiviral therapeutic to human patients.

* * * * *

UNITED STATES PATENT AND TRADEMARK OFFICE
CERTIFICATE OF CORRECTION

PATENT NO. : 5,503,828

DATED : April 2, 1996

INVENTOR(S) : Douglas Testa, Mei-June Liao, Katalin Ferencz-Biro, Abbas Rashidbaigi, Mario DiPaola, and Manisha Padhye It is certified that error appears in the above-identified patent and that said Letters Patent are hereby corrected as shown below:

Col. 10, line 17, delete "4x10" and insert thereof -- $4x10^6$ --.

Col. 14, line 14, delete "bully" and insert thereof -- buffy --.

Col. 14, line 25, delete "ix" and insert thereof -- 1x --.

Col. 16, in Table 2, delete the word "Spec." from line 23 and insert -- Spec. -- on line 25 above the word "Actvy" in column 6 of Table 2.

Col. 18, in Table 5, delete the word "AP" from line 10 and insert -- AP -- on line 12 above the word "Daudi" in column 5 of Table 5.

Col. 22, line 1, delete "cySteine" and insert thereof -- cysteine --.

Col. 25, line 26, delete "α516" and insert thereof -- α16 --.

Col. 31, in Table 16, line 57, delete "Lymph" and insert thereof -- Lymphopenia --.

Col. 34, in Table 16, line 8, delete the second occurrence of "10" and insert in place thereof -- 11 -- and in line 8, final column insert -- 10 --.

Col. 33, in Table 16, line 51, delete "75" from "Reference 4" column and insert -- 75 -- on line 51 under "Reference 9" column.

UNITED STATES PATENT AND TRADEMARK OFFICE
CERTIFICATE OF CORRECTION

PATENT NO. : 5,503,828
DATED : April 2, 1996
INVENTOR(S) : Douglas Testa, Mei-June Liao, Katalin Ferencz-Biro, Abbas Rashidbaigi, Mario DiPaola, and Manisha Padhye It is certified that error appears in the above-identified patent and that said Letters Patent are hereby corrected as shown below:

Col. 35, in Table 16, line 10, delete "20 MU/m$^{2/d}$" and insert thereof -- 20 MU/m$^2$/d --.

Col. 37, in Table 16, line 37, delete "MU/1/22" and insert thereof -- MU/m$^2$ --.

Col. 37, in Table 16, line 43, delete "Nyalgia" and insert thereof -- Myalgia --.

Col. 40, in Table 16, line 46, insert -- 104 -- under "Reference 15" column.

Col. 39, in Table 16, line 67, insert -- N -- under first column.

Col. 39, in Table 16, line 81, move "19" from "Reference 11" column and insert under "Reference 12" column.

Col. 40, in Table 16, line 81, move "4" from "Reference 14" column and insert under "Reference 15" column.

Col. 42, in Table 16, line 7, delete "FN-αn3" and insert thereof -- IFN-αn3 --.

Col. 42, in Table 16, line 29, delete "-2" and insert in place thereof -- ~2 --.

Col. 42, in Table 16, line 48, delete "-2" and insert thereof -- ~2 --.

Col. 42, in Table 16, line 66, delete "-2" and insert thereof -- ~2 --.

UNITED STATES PATENT AND TRADEMARK OFFICE
CERTIFICATE OF CORRECTION

PATENT NO. : 5,503,828
DATED : April 2, 1996
INVENTOR(S) : Douglas Testa, Mei-June Liao, Katalin Ferencz-Biro, Abbas Rashidbaigi, Mario DiPaola, and Manisha Padhye It is certified that error appears in the above-identified patent and that said Letters Patent are hereby corrected as shown below:

Col. 44, in Table 16, line 8, delete "-2" and insert thereof -- ~2 --.

Col. 44, in Table 16, line 30, delete "-2" and insert thereof -- ~2 --.

Col. 44, in Table 16, line 49, delete "-2" and insert thereof -- ~2 --.

Col. 44, in Table 16, line 70, delete "-2" and insert thereof -- ~2 --.

Col. 59, claim 1, line 34, delete "µ10" and insert thereof -- α10 --.

Col. 59, claim 1, line 34, delete "α116" and insert thereof -- α16 --.

Signed and Sealed this

Twenty-second Day of October, 1996

BRUCE LEHMAN

Commissioner of Patents and Trademarks